United States Patent [19]
Cerri et al.

[11] Patent Number: 5,583,127
[45] Date of Patent: Dec. 10, 1996

[54] 17-IMINOMETHYLALKENYL-5 β, 14 β-ANDROSTANE AND 17-IMINOALKYL-5 β, 14 β-ANDROSTANE DERIVATIVES ACTIVE ON THE CARDIOVASCULAR SYSTEM, AND PHARMACEUTICAL COMPOSITIONS CONTAINING SAME

[75] Inventors: Alberto Cerri, Gessate; Giuseppe Bianchi, Milan; Patrizia Ferrari, Varese; Elena Folpini, Milan; Piero Melloni, Bresso, all of Italy

[73] Assignee: Sigma-Tau Industrie Farmaceutiche Riunite S.p.A., Rome, Italy

[21] Appl. No.: 363,060

[22] Filed: Dec. 23, 1994

[30] Foreign Application Priority Data

Dec. 23, 1993 [DE] Germany ............ 43 44 236.6

[51] Int. Cl.[6] .......... A61K 31/57; A61K 31/575; A61K 31/58; C07J 9/00
[52] U.S. Cl. .......... 514/175; 514/174; 514/176; 514/182; 540/108; 540/109; 540/110; 540/112; 540/113; 552/540; 552/548; 552/554; 552/559; 552/563; 552/582
[58] Field of Search ............ 552/540, 548, 552/554, 559, 582, 563; 514/174, 175, 176, 182; 540/108, 109, 110, 112, 113

[56] References Cited

U.S. PATENT DOCUMENTS 4,689,410  8/1987  Barton et al. ............ 540/108

OTHER PUBLICATIONS

Lindig, et al., *Tetrahedron*, 28(6), pp. 1847–1858 (1972).
Krasso, et al., *Helv. Chim Acta*, 55(5), pp. 1352–1371 (1972).
Thomas, et al., *J. of Pharmac. & Exp. Ther.*, pp. 219–231 (1974).
Gelbart, et al., *J. of Med. Chem.*, 21(3), pp. 284–288 (1978).

*Primary Examiner*—Kimberly J. Kestler
*Attorney, Agent, or Firm*—Oblon, Spivak, McClelland, Maier & Neustadt, P.C.

[57] ABSTRACT

Disclosed are 17-iminomethylalkenyl and 17-iminoalkyl-14β-hydroxy-5β-androstane derivatives of the formula (I):

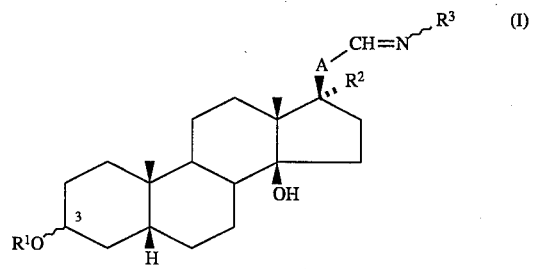

wherein the symbol ⁓ means α or β configuration or a Z or E configuration; A represents $(CH_2)_m$ or $-(CH=CH)_n-$; m represents an integer number from 1 to 6; n represents an integer number from 1 to 3; $R^2$ represents hydrogen or hydroxy; $R^1$ represents hydrogen, $C_2-C_4$ alkyl unsubstituted or substituted by $NR^4R^5$ wherein $R^4$ and $R^5$, which may be the same or different, represent hydrogen, $C_1-C_4$ alkyl or $R^4$ and $R^5$ may form, when taken together with the nitrogen atom, a five- or six- membered heterocyclic ring optionally containing one or more heteroatoms selected from oxygen and nitrogen; $R^3$ represents $NHC(=X)NR^6R^7$ or $OR^8$ wherein $R^6$ and $R^7$, which may be the same or different, represent hydrogen, methyl, or $C_2-C_4$ alkyl unsubstituted or substituted by $NR^4R^5$ wherein $R^4$ and $R^5$ have the previously defined meanings; $R^8$ represents hydrogen, methyl, $C_2-C_6$ alkyl, unsubstituted or substituted by one or more $NR^4R^5$ or $NHC(=NH)NH_2$, wherein $R^4$ and $R^5$ have the previously defined meanings; X represents O, S, or N⁓$R^9$; $R^9$ represents hydrogen, methyl, $C_2-C_4$ alkyl, $C_2-C_4$ acyl or phenyl, where the $C_2-C_4$ alkyl and $C_2-C_4$ acyl are unsubstituted or substituted by $NR^4R^5$, wherein $R^4$ and $R^5$ have the previously defined means; and $R^6$, $R^7$, and $R^9$, taken two by two, may form, together with the heteroatoms to which they are linked, a five- , six- , or seven-membered heterocyclic ring; or mixtures of α and β isomers at the 3-position; or mixtures of Z and E isomers of the group A—CH=N⁓$R^3$; or pharmaceutically acceptable salts thereof. The compounds are useful for the treatment of cardiovascular disorders, such as heart failure and hypertension. Also, disclosed is a process for preparing the derivatives by reaction of the corresponding 17-alkyl or 17-methylalkenyl aldehyde with a compound of the formula $H_2NNHC(=X)NR^6R^7$ or $H_2NOR^8$.

3 Claims, No Drawings

17-IMINOMETHYLALKENYL-5 β, 14 β-ANDROSTANE AND 17-IMINOALKYL-5 β, 14 β-ANDROSTANE DERIVATIVES ACTIVE ON THE CARDIOVASCULAR SYSTEM, AND PHARMACEUTICAL COMPOSITIONS CONTAINING SAME

The present invention relates to new 17-iminomethylalkenyl- and 17-iminoalkyl-14β-hydroxy-5β-androstane derivatives active on the cardiovascular system, to a process for their preparation and to pharmaceutical compositions containing same for the treatment of cardiovascular disorders, such as heart failure and hypertension.

The known 17β-guanidinoiminomethyl-5β-androstane-3β,14β-diol and 17-guanidinoimino-5β-androstane-3β,14β-diol are reported to be weak inhibitors of $Na^{+,K+}$-ATPase and weak positive inotropic agents (Gelbart A. and Thomas R., J. Med. Chem., 1978, 21, 284; Schönfeld W. and Repke K., Quant. Struct. Act. Relat., 1988, 7, 160). Other substituted 17β-hydrazonomethyl-5β-androstane-3β, 14β-diols (ureido-imino and hydrazono) are reported not to inhibit $Na^+$, $K^+$-ATPase (Thomas R. et al., J. Pharmacol. Exp. Ther., 1974, 191, 219; Boutagy J. et al., Aust. J. Pharm. Sci, 1973, 2, 41).

The compounds of the present invention have general formula (I):

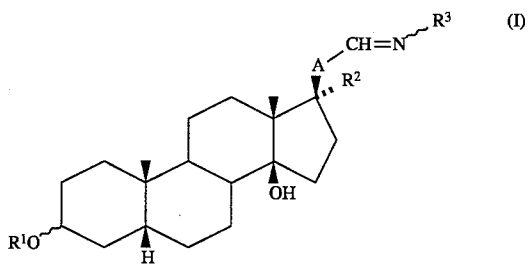

wherein:
the symbol ⁓ means α or β configuration or a Z or E configuration;
A represents $(CH_2)_m$ or $-(CH=CH)_n-$;
m represents an integer number from 1 to 6;
n represents an integer number from 1 to 3.
$R^1$ represents hydrogen, C2–C4 alkyl unsubstituted or substituted by $NR^4R^5$ wherein $R^4$, $R^5$ which may be the same or different, represent hydrogen, C1–C4 alkyl or $R^4$ and $R^5$ may form, taken together with the nitrogen atom, a five- or six-membered heterocyclic ring optionally containing one or more further heteroatoms selected from oxygen and nitrogen;
$R^2$ represents hydrogen or hydroxy;
$R^3$ represents $NHC(=X)NR^6R^7$ or $OR^8$ wherein
$R^6$, $R^7$ which may be the same or different, represent hydrogen, methyl or C2–C4 alkyl unsubstituted or substituted by $NR^4R^5$ wherein $R^4$ and $R^5$ have the previously defined meanings;
$R^8$ represents hydrogen; methyl; C2–C6 alkyl, unsubstituted or substituted by one or more $NR^4R^5$ or $NHC(=NH)NH_2$, wherein $R^4$ and $R^5$ have the previously defined meanings;
X represents O, S or N⁓$R^9$;
$R^9$ represents hydrogen, methyl, C2–C4 alkyl, C2–C4 acyl or phenyl, where the C2–C4 alkyl, C2–C4 acyl are unsubstituted or substituted by $NR^4R^5$, wherein $R^4$ and $R^5$ have the previously defined meanings; and
$R^6$, $R^7$, $R^9$ taken two by two may form, together with the heteroatoms they are linked to, and where possible, a five- or six- or seven-membered heterocyclic ring.

Where the compounds of formula (I) can exhibit tautomerism, the formula is intended to cover all tautomers; the invention encompasses within its scope all the possible steroisomers, Z and E isomers and their mixtures, optical isomers and their mixtures, the metabolites and the metaboic precursors of compound of formula (I).

Also the pharmaceutical acceptable salts are included in the scope of the invention. Pharmaceutical acceptable salts are salts which retain the biological activity of the base and are derived from such known pharmacologically acceptable acids such as, e. g., hydrochloric, hydrobromic, sulfuric, phosphoric, fumaric, succinic, oxalic, malic, tartaric, maleic, citric, methanesulfonic or benzoic acid and others commonly used in the art.

The compounds of the invention also include solvates (e.g. hydrates).

N-oxides, where the nitrogen atom is not substituted with a hydrogen atom, are also encompassed by the invention.

The alkyl groups are branched or straight chain groups or cyclic groups.

The C2–C4 alkyl is preferably ethyl, n-propyl, iso-propyl, n-butyl or tert-butyl.

The C1–C4 alkyl is preferably methyl, ethyl, n-propyl, iso-propyl, n-butyl, tert-butyl.

The C2–C4 acyl is preferably acetyl, propionyl, n-butyryl or iso-butyryl.

The $R^1$ group is preferably hydrogen, 2-aminoethyl, 3-amino-propyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl.

The $NR^6R^7$ group is preferably amino, methylamino, dimethylamino, diethylamino, iso-propylamino, pyrrolidinyl, piperidyl, morfolino, piperazin-1-yl, 4-methylpiperazin-1-yl, 4-(2-hydroxyethyl)-piperazin-1-yl, 4-(2-dimethylaminoethyl)piperazin-1-yl, 2-dimethylaminoethylamino, 2-diethylaminoethylamino, (2-dimethylaminoethyl)methylamino, (2-diethylaminoethyl)methylamino, 3-dimethylaminopropylamino, (3-dimethylaminopropyl)methylamino, 2-(1-pyrrolidinyl)ethylamino, 3-(1-pyrrolidinyl)propylamino, (2-(1-pyrrolidinyl)ethyl)methylamino.

The $R^8$ group is preferably hydrogen, methyl, 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl, 2-guanidinoethyl, 3-guanidinopropyl.

The $R^9$ group is preferably hydrogen, methyl, 2-aminoethyl, 3-aminopropyl, 2-dimethylaminoethyl, 3-dimethylaminopropyl, 2-(1-pyrrolidinyl)ethyl, 3-(1-pyrrolidinyl)propyl, acetyl, phenyl.

$R^6$ and $R^9$ groups taken together with the heteroatom they are linked to, are preferably 2-imidazolin-2-yl, 1-methyl-2-imidazolin-2-yl, 5-oxo-2-imidazonlin-2-yl, 1-methyl-5-oxo-2-imidazolin-2-yl, 2-imidazolyl, 2-(1-methyl)imidazolyl, 1,4,5,6-tetrahydro-2-pyrimidinyl, 1-methyl-1,4,5,6-tetrahydro-2-pyrimidinyl, 1,4,5,6-tetrahydro-6-oxo-2-pyrimidinyl or 1-methyl-1,4,5,6-tetrahydro-6-oxo-2-pyrimidinyl.

Preferred examples of specific compounds according to the present invention are (E,E)-17β-(3-guanidinoimino-1-propenyl)-5β-androstane-3β,14β-diol (E,E)-17β-[3-(3-methylguanidinoimino)-1-propenyl]-5β-androstane-3β,14β-diol (E,E)-17β-[3-(3,3-dimethylguanidinoimino)-1-propenyl]-5β-androstane-3β,14β-diol (E,E)-17β-[3-(2-imidazolin-2-yl)hydrazono-1-propenyl]-5β-androstane-3β,14β-diol (E,E)-17β-[3-(1-methyl-2-imidazolin-2-yl)hydrazono-1-propenyl]-5β-androstane-3β,14β-diol (E,E)-17β-[3-5-oxo-2-imidazolin-2-yl)hydrazono-1-propenyl]-5β-androstane-3β,14β-diol (E,E)-17β-[3-(2-imidazolyl)hydrazono-1-propenyl]-5β-androstane-3β,14β-diol (E,E)-17β-[3-(1,4,5,6-tetrahydro-2-pyrimidinyl)hydrazono-1-propenyl]-5β-androstane-3β,14β-diol (E,E)-17β-(3-[3-(2-dimethylaminoethyl)guanidinoimino]-1-propenyl)-5β-androstane-3β,14β-diol (E,E)-17β-[3-(3-phenyl)guanidinoimino-1-propenyl]-5β-androstane-3β,14β-diol (E,E)-17β-(3-semicarbazono-1-propenyl)-5β-androstane-3β,14β-diol (E,E)-17β-(3-thiosemicarbazono-1-propenyl)-5β-androstane-3β,14β-diol (E,E)-17β-(3-hydroxyimino-1-propenyl)-5β-androstane-3β,14β-diol (E,E)-17β-(3-methoxyimino-1-propenyl)-5β-androstane-3β,14β-diol (E,E)-17β-[3-(2-aminoethoxyimino)-1-propenyl]-5β-androstane-3β,14β-diol (E,E)-17β-[3-aminopropoxyimino)-1-propenyl]-5β-androstane-3β,14β-diol (E,E)-17β-[3-(2-dimethylaminoethoxyimino)-1-propenyl]-5β-androstane-3β,14β-diol (E,E)-17β-[3-(3-dimethylaminopropoxyimino)-1-propenyl]-5β-androstane-3β,14β-diol (E,E)-17β-[3-(2-guanidinoethoxyimino)-1-propenyl]-5β-androstane-3β,14β-diol (E,E)-17β-[3-(3-guanidinopropoxyimino)-1-propenyl]-5β-androstane-3β,14β-diol (E,E,E)-17β-(5-guanidinoimino-1,3-pentadienyl)-5β-androstane-3β,14β-diol (E,E,E)-17β-[5-(3-methylguanidinoimino)-1,3-pentadienyl]-5β-androstane-3β,14β-diol (E,E,E)-17β-[5-(3,3-dimethylguanidinoimino)-1,3-pentadienyl]-5β-androstane-3β,14β-diol (E,E,E)-17β-[5-(2-imidazolin-2-yl)hydrazono-1,3-pentadienyl]-5β-androstane-3β,14β-diol (E,E,E)-17β-[5-(1-methyl-2-imidazolin-2-yl)hydrazono-1,3-pentadienyl]-5β-androstane-3β,14β-diol (E,E,E)-17β-[5-(5-oxo-2-imidazolin-2-yl)hydrazono-1,3-pentadienyl]-5β-androstane-3β,14β-diol (E,E,E)-17β-[5-(2-imidazoly)hydrazono-1,3-pentadienyl]-5β-androstane-3β,14β-diol (E,E,E)-17β-[5-(1,4,5,6-tetrahydro-2-pyrimidinyl)hydrazono-1,3-pentadienyl]-5β-androstane-3β,14β-diol (E,E,E)-17β-{5-[3-(2-dimethylaminoethyl)guanidinoimino]-1,3-pentadienyl}-5β-androstane-3β,14β-diol (E,E,E)-17β-[5-(3-phenylguanidinoimino)-1,3-pentadienyl]-5β-androstane-3β,14β-diol (E,E,E)-17β-(5-semicarbazono-1,3-pentadienyl)-5β-androstane-3β,14β-diol (E,E,E)-17β-(5-thiosemicarbazono-1,3-pentadienyl)-5β-androstane-3β,14β-diol (E,E,E)-17β-(5-hydroxyimino-1,3-pentadienyl)-5β-androstane-3 β,14β-diol (E,E,E)-17β-(5-methoxyimino-1,3-pentadienyl)-5β-androstane-3β,14β-diol (E,E,E)-17β-[5-(2-aminoethoxyimino)-1,3-pentadienyl]-5β-androstane-3β,14β-diol (E,E,E)-17β-[5-(3-aminopropoxyimino)-1,3-pentadienyl]-5β-androstane-3β,14β-diol (E,E,E)-17β-[5-(2-dimethylaminoethoxyimino)-1,3-pentadienyl]-5β-androstane-3β,14β-diol (E,E,E)-17β-[5-(3-dimethylaminopropoxyimino)-1,3-pentadienyl]-5β-androstane-3β,14β-diol (E,E,E)-17β-[5-(2-guanidinoethoxyimino)-1,3-pentadienyl]-5β-androstane-3β,14β-diol (E,E,E)-17β-[5-(3-guanidinopropoxyimino)-1,3-pentadienyl]-5β-androstane-3β,14β-diol (E)-17β-(2-guanidinoimino)ethyl-5β-androstane-3β,14β-diol (E)-17β-[2-(3-methylguanidinoimino)ethyl]-5β-androstane-3β,14β-diol (E)-17β-[2-(3,3-dimethylguanidinoimino)ethyl]-5β-androstane-3β,14β-diol (E)-17β-[2-(2-imidazolin-2-yl)hydrazonoethyl]-5β-androstane-3β,14β-diol (E)-17β-[2-(1-methyl-2-imidazolin-2-yl)hydrazonoethyl]-5β- androstane-3β,14β-diol (E)-17β-[2-(5-oxo-2-imidazolin-2-yl)hydrazonoethyl]-5β-androstane-3β,14β-diol (E)-17β-[2-(2-imidazolyl)hydrazonoethyl]-5β-androstane-3β,14β-diol (E)-17β-[2-(1,4,5,6-tetrahydro-2-pyrimidinyl)hydrazonoethyl]-5β-androstane-3β,14β-diol (E)-17β-{2-[3-(2-dimethylaminoethyl)guanidinoimino]ethyl}-5β-androstane-3β,14β-diol (E)-17β-[2-(3-phenylguanidinoimino)ethyl]-5β-androstane-3β,14β-diol (E)-17β-(2-semicarbazonoethyl)-5β-androstane-3β,14β-diol (E)-17β-(2-thiosemicarbazonoethyl)-5β-androstane-3β,14β-diol (E)-17β-(2-hydroxyiminoethyl)-5β-androstane-3β,14β-diol (E)-17β-(2-methoxyiminoethyl)-5β-androstane-3β,14β-diol (E)-17β-[2-(2-aminoethoxyimino)ethyl]-5β-androstane-3β,14β-diol (E)-17β-[2-(3-aminopropoxyimino)ethyl]-5β-androstane-3β,14β-diol (E)-17β-[2-(2-dimethylaminoethoxyimino)ethyl]-5β-androstane-3β,14β-diol (E)-17β-[2-(3-dimethylaminopropoxyimino)ethyl]-5β-androstane-3β,14β-diol (E)-17β-[2-(2-guanidinoethoxyimino)ethyl]-5β-androstane-3β,14β-diol (E)-17β-[2-(3-guanidinopropoxyimino)ethyl]-5β-androstane-3β,14β-diol (E)-17β-(3-guanidinoiminopropyl)-5β-androstane-3β,14β-diol (E)-17β-[3-(3-methylguanidinoimino)propyl]-5β-androstane-3β,14β-diol (E)-17β-[3-(3,3-dimethylguanidinoimino)propyl]-5β-androstane-3β,14β-diol (E)-17β-[3-(2-imidazolin-2-yl)hydrazonopropyl]-5β-androstane-3β,14β-diol (E)-17β-[3-(2-imidazolyl)hydrazonopropyl]-5β-androstane-3β,14β-diol (E)-17β-[3-(1-methyl-2-imidazolin-2-yl)hydrazonopropyl]-5β-androstane-3β,14β-diol (E)-17β-[3-(5-oxo-2-imidazolin-2-yl)hydrazonopropyl]-5β-androstane-3β,14β-diol (E)-17β-[3-(1,4,5,6-tetrahydro-2-pyrimidinyl)hydrazonopropyl]-5β-androstane-3β,14β-diol (E)-17β-{3-[3-(2-dimethylaminoethyl)guanidinoimino]propyl}-5β-androstane-3β,14β-diol (E)-17β-[3-(3-phenylguanidinoimino)propyl]-5β-androstane-3β,14β-diol (E)-17β-(3-semicarbazonopropyl)-5β-androstane-3β,14β-diol (E)-17β-(3-thiosemicarbazonopropyl)-5β-androstane-3β,14β-diol (E)-17β-(3-hydroxyiminopropyl)-5β-androstane-3β,14β-diol (E)-17β-(3-methoxyiminopropyl)-5β-androstane-3β,14β-diol (E)-17β-[3-(2-aminoethoxyimino)propyl]-5β-androstane-3β,14β-diol (E)-17β-[3-(3-aminopropoxyimino)propyl]-5β-androstane-3β,14β-diol (E)-17β-[3-(2-dimethylaminoethoxyimino)propyl]-5β-androstane-3β,14β-diol (E)-17β-[3-(3-dimethylaminopropoxyimino)propyl]-5β-androstane-3β,14β-diol (E)-17β-[3-(2-guanidinoethoxyimino)propyl]-5β-androstane-3β,14β-diol (E)-17β-[3-(3-guanidinopropoxyimino)propyl]-5β-androstane-3β,14β-diol and where there are the (E) isomers also the corresponding (Z) isomers and their mixtures;

and the corresponding 17α-hydroxy compounds of the compounds mentioned above;

and the corresponding 3β-(3-aminopropyl), 3β-(3-dimethylaminopropyl), 3β-(3-diethylaminopropyl), 3β-(3-(1-pyrrolidinyl)propyl), 3β-(2-aminoethyl), 3β-(2-dimethylaminoethyl), 3β-(2-diethylaminoethyl) and 3β-(2-(1-pyrrolidinyl)ethyl) ethers of the compounds mentioned above;

and the corresponding 3α-hydroxy compounds of the 3β-hydroxy derivatives;

and the corresponding 3α-(3-aminopropyl), 3α-(3-dimethylaminopropyl), 3α-(3-diethylaminopropyl), 3α-(3-(1-pyrrolidinyl)propyl), 3α-(2-aminoethyl), 3α-(2-dimethylaminoethyl), 3α-(2-diethylaminoethyl) and 3α-(2-(1-pyrrolidinyl)ethyl) ethers of the compounds mentioned above.

The invention furthermore provides a process for the preparation of compounds of general formula (I), which comprises a condensation reaction of compounds of formula (II)

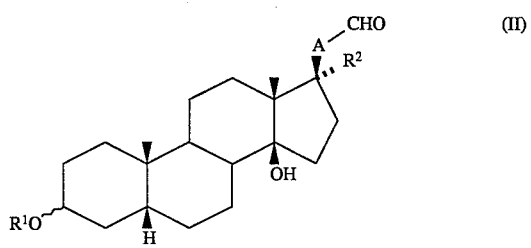

in which A, R$^1$, R$^2$ and the symbol ⁓ are as above defined, with a compound of general formula (III) and (IV)

H$_2$NNHC(=X)NR$^6$R$^7$ (III)
H$_2$NOR$^8$ (IV)

to give compounds of general formula (I), Compounds (III) and (IV) can be used as the free base or in the form of a salt with an acid such as, e.g., hydrochloric, carbonic, oxalic, hydiodic or sulfuric acid. The reaction can be carried out in a solvent, such as ethanol, methanol, acetonitrile, dioxane, tetrahydrofuran, water or a mixture of said solvents, at a temperature between 0° C. and the boiling point of the solvents mentioned above or of their mixtures. To the reaction mixtures, additional salts, such as, e.g., NaH$_2$PO$_4$, Na$_2$HPO$_4$NaOAc, can be added as well as acids such as, e.g., hydrochloric, hydrobromic, sulfuric, acetic, phosphoric acid, and bases such as, e.g., sodium or potassium hydroxide, to maintain the desired pH.

The groups optionally present in R$^1$ and/or R$^2$ are protected, if necessary, by known methods, to give after removal by known methods of protective groups, if any, compounds of general formula (I) which can be converted into other compounds of general formula (I) by known methods.

Compounds of general formula (II) in which A is —(CH=CH)—, R$^1$ and R$^2$ are hydrogen and the symbol ⁓ means a β configuration, is a known compound (Fullerton D. S. et al., J. Med. Chem., 1976, 19, 1330).

Unknown compounds of general formula (II) are prepared with methods well known to those skilled in the art.

For example compounds of general formula (II) in which A is —(CH=CH)$_n$—, where n is an integer number from 1 to 2, R$^1$ and R$^2$ are hydrogen and the symbol ⁓ means α or β configuration, are prepared from the known 3β,14β-dihydroxy-5β-androstane-17β-carboxaldehyde (Boutagy J. and Thomas R., Aust. J. Chem., 1971, 24, 2723) and the unknown 3α,14β-dihydroxy-5β-androstane-17β-carboxaldehyde by reaction with trimethyl phosphonoacetate or triethyl (E)-4-phosphonocrotonate in the presence of a base, followed by reduction of the ester function to the corresponding alcohol and subsequent allylic oxidation to the unsaturated aldehyde. The sequence can be repeated on the proper unsaturated aldehyde to obtain the compound of general formula (II) where n is 3, R$^1$ and R$^2$ are hydrogen and the symbol ⁓ means α or β configuration.

For example compound of general formula (II) in which A is —(CH=CH)$_n$—, where n is 1, R$^1$ is hydrogen, R$^2$ is hydroxy and the symbol ⁓ means α or β configuration, is prepared from the known methyl (E)-3β,14β-dihydroxy-5β-pregn-20-ene-21-carboxylate (Boutagy J. and Thomas R., Aust. J. Pharm. Sci., 1972, NS1,67) or from the unknown methyl (E)-3α,14β-dihydroxy-5β-pregn-20-ene-21-carboxylate by allylic oxidation, for example with selenium dioxide, followed by reduction of the ester function to the corrisponding alcohol and subsequent allylic oxidation to the unsaturated aldehyde. By reaction of this compound with trimethyl phosphonoacetate or triethyl (E)-4-phosphonocrotonate in the presence of a base, followed by reduction of the ester function to the corrisponding alcohol and subsequent allylic oxidation to the unsaturated aldehyde, compounds of general formula (II) in which A is —(CH=CH)$_n$—, where n is 2 or 3, R$^1$ is hydrogen, R$^2$ is hydroxy and the symbol ⁓ means α or β configuration, are prepared.

For example compounds of general formula (II) in which A is —(CH$_2$)$_m$—, where m is 2, 4 or 6, R$^1$ is hydrogen, R$^2$ is hydrogen or hydroxy and the symbol ⁓ means α or β configuration, are prepared from the corresponding compounds of general formula (II) in which A is —(CH=CH)$_n$—, where n is 1, 2 or 3, R$^1$ is hydrogen, R$^2$ is hydrogen or hydroxy and the symbol ⁓ means α or β configuration, by hydrogenation over a catalyst chosen, for example, among palladium, platinum or Raney Nickel.

Compounds of general formula (II) in which A is —(CH$_2$)$_m$—, where m is 1, 3 or 5, R$^1$ is hydrogen, R$^2$ is hydrogen or hydroxy and the symbol ∽ means α or β configuration, are prepared from the corresponding compounds of general formula (II) in which A is —$(CH_2)_m$— where m is 0, 2 or 4; for example, by elongation with methoxymethyltriphenylphosphonium chloride in the presence of a base and successive acid hydrolysis; for example by treatment with nitromethane in the presence of a base, subsequent acetilation and reduction of the acetoxy group, followed by transformation of the nitro group to the nitrile and final reduction to the desired aldehyde.

For example the unknown 3α-hydroxy compounds are prepared from the corresponding known 3-keto compounds by reduction with sodium borohydride, lithium aluminumhydride or lithium aluminum-tri-tert-butoxyhydride. The corresponding unknown 3-keto compounds are obtained from the 3β-hydroxy derivative by oxidation with known methods such as Jones reagent, chromic anhydride in pyridine or tetrapropylammonium perruthenate and N-methylmorpholine N-oxide.

Compounds (II) in which A is $(CH_2)_m$, where m is an integer number from 1 to 6, —$(CH=CH)_n$—, where n is an integer number from 1 to 3, $R^2$ is hydrogen or hydroxy and the symbol ∽ means an α or β configuration and where $R^1$ is different from hydrogen, are prepared from the corresponding compounds (II) where $R^1$ is hydroxy by reaction with a compound of formula (V)

$$R^{10}W \qquad (V)$$

where $R^{10}$ is as defined for $R^1$, but different from hydrogen, or a group convertible to $R^1$ and W is an electron-withdrawing group, such as halogen, mesyloxy, or tosyloxy group, which confers electrophilic properties to the attached carbon atom, and $R^1$ is as above defined. The reaction is best carried out in an inert aprotic solvent, such as tetrahydrofuran, dioxane, dimethylformamide, dimethyl-sulfoxyde or in neat $R^{10}W$ and in the presence of a base, e.g. sodium or potassium hydride, at a temperature ranging from 0° C. to 110° C.

In all the transformations mentioned above the hydroxy group optionally present in $R^2$ and the aldehydic function are protected, if necessary, by known methods to give, after removal by known methods of protective groups, if any, a compound of general formula (II).

Compounds of general formula (III), (IV) and (V) are known compounds, generally commercially available or preparable from known compounds by known methods.

Compounds of general formula (I) prepared according to the invention and their pharmaceutically acceptable salts are useful agents for the treatment of cardiovascular disorders such as heart failure and hypertension.

Compounds of general formula (I) prepared according to the invention and their pharmaceutically acceptable salts have reduced toxicity compared to known positive inotropic agents such as ouabain and digitoxin.

Moreover said compounds (I) show good affinity for the receptor site of the $Na^+, K^+$-ATPase.

To test the affinity for the receptor site of the $Na^+, K^+$-ATPase and the agonist or antagonist activity on the enzyme, the following tests were used:

a) displacement of the specific $^3H$-ouabain binding from the $Na^+, K^+$-ATPase receptor purified according to Jorghensen (Jorghensen P., BBA, 1974, 356, 36) and Erdmann (Erdmann E. et al., *Arzneim. Forsh*, 1984, 34, 1314);

b) inhibition of the activity of the purified $Na^+, K^+$-ATPase measured as % of hydrolysis of $^{32}P$-ATP in presence and in absence of the tested compound (Doucet A. et al., *Am. J. Physiol.*, 1986, 251, F851)

Systolic blood pressure (SBP) and heart rate (HR) were measured, by the tail cuff method, in young prehypertensive male rats (MHS or SHR) strains before the development of hypertension (4 weeks of age) for recording the basal values of SBP. Groups of 7 rats were formed and subdivided in control and treated groups. The compound, suspended in Methocel 0.5% (w/v), was orally given daily for at least 5 weeks to the treated groups. The control group received only Methocel.

SBP and HR were measured weekly 6 and 24 hrs after treatment. After 5 weeks of treatment, when hypertension was fully developed in the control group (9 weeks of age), washout was started for at least one week, to verify whether the treatment maintained blood pressure low or reestablished the basal values.

The validity of this procedure for detecting an hypotensive activity, had been previously tested for β blockers, which did not produce any hypotensive effect when acutely given to hypertensive rats (SHR), but were effective in preventing the development of hypertension when administered starting from weaning for more than 5 weeks. (Takeda K. et al., *Japan J. Pharmacol.*, 1979, 29,171; Takeda K. et al. *Japan J. Pharmacol.*, 1982, 32, 283; Richer C. et al. *Eur. J. Pharmacol*, 1978, 47,393).

The affinity and the inhibitory activity of some compounds in the two tests are shown in the following table:

|  | Binding $^3H$-Ouab. Displacement -log $IC_{50}$ | Inhibitory Activity -log $IC_{50}$ |
| --- | --- | --- |
| Comp. I-aa | 7.6 | 6.8 |
| Comp. I-ab | 6.5 | 5.5 |
| Comp. I-ac | 7.3 | 5.6 |
| Comp. I-ad | 6.2 | 5.2 |
| Comp. I-ae | 6.8 | 5.6 |
| Comp. I-af | 5.7 | 4.4 |
| Comp. I-ag | 7.4 | 5.8 |
| Comp. I-ah | 6.1 | 5.1 |
| Comp. I-ai | 6.6 | 5.5 |
| Comp. I-aj | 6.0 | 5.0 |
| Comp. I-ak | 5.7 | 4.6 |
| Comp. I-al | 5.4 | 4.4 |
| Comp. I-am | 5.6 | 4.6 |
| Comp. I-an | 5.7 | 4.7 |
| Comp. I-ao | 7.8 | 7.7 |
| Comp. I-ap | 7.3 | 7.0 |
| Comp. I-aq | 7.6 | 7.5 |
| Comp. I-ar | 7.2 | 6.9 |
| Comp. I-as | 7.0 | 6.8 |
| Comp. I-at | 6.8 | 6.5 |
| Comp. I-au | 6.3 | 5.1 |
| Comp. I-av | 6.0 | 5.0 |
| Comp. I-aw | 5.8 | 4.8 |
| Comp. I-bc | 7.1 | 6.4 |
| Comp. I-bd | 6.9 | 6.2 |
| Comp. I-bf | 7.6 | 6.5 |
| Comp. I-bg | 7.3 | 6.4 |
| Comp. I-bh | 7.4 | 6.2 |
| Comp. 1-bi | 6.9 | 5.7 |
| Comp. I-bj | 6.6 | 5.5 |
| Comp. I-bm | 7.6 | 7.1 |
| Comp. I-bn | 7.6 | 7.0 |
| Comp. 1-bo | 6.3 | 5.0 |
| Comp. I-bp | 6.2 | 5.1 |
| Comp. I-bt | 6.1 | 5.0 |
| Comp. I-bx | 7.7 | 6.9 |
| Comp. I-by | 7.7 | 7.5 |
| Comp. I-bz | 7.6 | 7.0 |
| Comp. I-ca | 7.5 | 7.4 |
| Comp. I-cb | 7.7 | 7.0 |

-continued

| Compound | Binding $^3$H-Ouab. Displacement -log IC$_{50}$ | Inhibitory Activity -log IC$_{50}$ |
| --- | --- | --- |
| Comp. I-cc | 7.7 | 7.5 |
| qomp. I-cd | 7.8 | 7.1 |
| Comp. 1-ce | 7.8 | 7.7 |
| Comp. I-cg | 7.5 | 7.0 |
| Comp. I-ci | 7.3 | 6.8 |
| Comp. I-ej | 7.3 | 6.5 |
| Comp. I-ck | 7.3 | 7.2 |
| Comp. I-cm | 7.0 | 6.0 |

The activity of some new compound in preventing the development of hypertension is shown in the following table:

EFFECT OF 5 WEEK-TREATMENT IN SPONTANEOUS HYPERTENSIVE RATS (MHS) ON THE DEVELOPMENT OF HYPERTENSION

| Compound | RATS | DOSE* mg/Kg/os | SBP mm Hg | HR beats/min. |
| --- | --- | --- | --- | --- |
| Controls | 7 | Methocel | 172 +/– 3.5 | 380 +/– 9.0 |
| Comp. I-aa | 7 | 10 | 149 +/– 3.9 | 373 +/– 10.0 |
| Comp. I-bz | 7 | 10 | 151 +/– 4.8 | 381 +/– 4.3 |

*in Methocel 0.5% w/v

The following examples illustrate the invention without limiting it.

EXAMPLE 1

(E,E)-17β-(3-Guanidinoimino-1-propenyl)-5β-androstane-3β,14β-diol (I-aa)

A mixture of 1.05 g of aminoguanidine hydrogencarbonate in 23 ml of water and 70 ml of dioxane was made acid to pH 3 with 3N HCl. A solution of 2.08 g of (E)-3β,14β-dihydroxy-5β-pregn-20-ene-21-carboxaldehyde (Fullerton D. S. et al., *J. Med. Chem.*, 1976, 19, 1330) in 20 ml of dioxane was added at room temperature. After 3 days the mixture was evaporated to dryness under reduced pressure. The crude product was purified by flash chromatography (SiO$_2$) using chloroform/methanol/28% ammonium hydroxide 80/20/3 as the eluant; the fractions containing the title compound were collected and evaporated to dryness. The residue was ground with diethyl ether and ethanol to give 1.58 g of the title compound (I-aa) as a white solid.

$^1$H-NMR (300 MHz, CD$_3$OD, ppm from TMS): 0.86 (3H, s); 0.97 (3H, s); 2.22–2.32 (1H, m); 4.05 (1H, s); 5.98 (1H, dd); 6.18 (1H, dd); 7.63 (1H, d).

EXAMPLE 2

17β-[3-(Z)-Guanidinoimino-1-(E)-propenyl]-5β-androstane-3β,14β-diol (I-ab)

The title compound (I-ab) (0.08 g) was a by product of the reaction described in Ex. 1 and was isolated as a white solid.

$^1$H-NMR (300 MHz, CD$_3$OD, ppm from TMS): 0.87 (3H, s); 0.97 (3H, s); 2.25–2.35 (1H, m); 4.05 (1H, s); 6.30 (1H, dd); 6.65 (1H, dd); 7.15 (1H, d).

EXAMPLE 3

(E,E)-17β-[3-(2-Imidazolin-2-yl)hydrazono-1-propenyl]-5β-androstane-3β,14β-diol (I-ac)

A solution of 1.19 g of 2-hydrazino-2-imidazoline hydrobromide in 20 ml of water and 60 ml of dioxane was made acid to pH 3 with 0.1N HBr. A solution of 2.08 g of (E)-3β,14β-dihydroxy-5β-pregn-20-ene-21-carboxaldehyde (Fullerton D. S. et al., *J. Med. Chem.*, 1976, 19, 1330) in 25 ml of dioxane was added at room temperature. After 3 days, the solution was evaporated to dryness under reduced pressure. The crude product was purified by flash chromatography (SiO$_2$) using chloroform/methanol/28% ammonium hydroxide 90/10/1 as the eluant; the fractions containing the title compound were collected and evaporated to dryness. The residue was ground with ethyl acetate and ethanol to give 1.54 g of the title compound (I-ac) as a white solid.

$^1$H-NMR (300 MHz, CD$_3$OD, ppm from TMS): 0.83 (3H, s); 0.98 (3H, s); 2.20–2.35 (1H, m); 3.50 (4H, s); 4.05 (1H, s); 5.97 (1H, dd); 6.20 (1H, dd); 7.65 (1H, d).

EXAMPLE 4

17β-[3-(Z)-(2-Imidazolin-2-yl)hydrazono-1-(E)-propenyl]-5β-androstane-3β,14β-diol (I-ad)

The title compound (I-ad) (0.14 g) was a by product of the reaction described in Ex. 1 and was isolated as a white solid.

$^1$H-NMR (300 MHz, CD$_3$OD, ppm from TMS): 0.85 (3H, s); 0.98 (3H, s); 2.27–2.37 (1H, m); 3.51 (4H, s); 4.05 (1H, s); 6.28 (1H, dd); 6.59 (1H, dd); 6.95 (1H, d).

EXAMPLE 5

(E,E)-17β-[3-(1-Methyl-2-imidazolin-2-yl)-hydrazono-1-propenyl]-5β-androstane-3β,14β-diol (I-ae)

The title compound (I-ae) (0.82 g) was obtained as a white solid, starting from (E)-3β,14β-dihydroxy-5β-pregn-20-ene-21-carboxaldehyde (1.04 g) (Fullerton D. S. et al., *J. Med. Chem.*, 1976, 19, 1330) and 1-methyl-2-hydrazino-2-imidazoline hydroiodide (prepared from 2-methylthio-1-methyl-2-imidazoline hydroiodide and hydrazine following the procedure described in Houben-Weil, Metoden der Organischen Chemie, Band VIII, Page 183) using the same procedure described in Ex. 1.

$^1$H-NMR (300 MHz, CD$_3$OD, ppm from TMS): 0.84 (3H, s); 0.99 (3H, s); 2.20–2.35 (1H, m); 3.00 (3H, s); 3.53 (4H, s); 4.05 (1H, s); 5.98 (1H, dd); 6.21 (1H, dd); 7.66 (1H, d).

EXAMPLE 6

(E,E)-17β-[3-(5-Oxo-2-imidazolin-2-yl)hydrazono-1-propenyl]-5β-androstane-3β,14β-diol (I-af)

The title compound (I-af) (0.78 g) was obtained as a white solid, starting from (E)-3β,14β-dihydroxy-5β-pregn-20-ene-21-carboxaldehyde (1.04 g) (Fullerton D. S. et al., *J. Med. Chem.*, 1976, 19, 1330) and 5-oxo-2-hydrazino-2-imidazoline hydroiodide (prepared from 2-methylthio-5-oxo-2-imidazoline hydroiodide and hydrazine following the procedure described in Houben-Well, Metoden der Organischen Chemie, Band VIII, page 183) using the same procedure described in Ex. 1.

¹H-NMR (300 MHz, CD₃OD, ppm from TMS): 0.84 (3H, s); 0.98 (3H, s); 2.30–2.40 (1H, m); 3.60 (1H, d); 3.82 (1H, d); 4.05 (1H, s); 5.95 (1H, dd); 6.18 (1H, dd); 7.12 (1H, d).

EXAMPLE 7

(E,E)-17β-[3-(1,4,5,6-Tetrahydro-2-pyrimidinyl)-hydrazono-1-propenyl]-5β-androstane-3β,14β-diol (I-ag)

The title compound (I-ag) (0.75 g) was obtained as a white solid, starting from (E)-3β,14β-dihydroxy-5β-pregn-20-ene-21-carboxaldehyde (1.04 g) (Fullerton D. S. et al., *J. Med. Chem.*, 1976, 19, 1330) and 2-hydrazino-1,4,5,6-tetrahydro-2-pyrimidine hydroiodide (prepared from 2-methylthio-1,4,5,6-tetrahydro-2-pyrimidine hydroiodide and hydrazine following the procedure described in Houben-Weil, Metoden der Organischen Chemie, Band VIII, page 183) using the same procedure described in Ex. 1.

¹H-NMR (300 MHz, CD₃OD, ppm from TMS): 0.82 (3H, s); 0.98 (3H, s); 2.25–2.35 (1H, m); 3.14 (4H, m); 4.05 (1H, s); 5.95 (1H, dd); 6.18 (1H, dd); 7.59 (1H, d).

EXAMPLE 8

17β-[3-(Z)-(1,4,5,6-Tetrahydro-2-pyrimidinyl)-hydrazono-1-(E)-propenyl]-5β-androstane-3β,14β-diol (I-ah)

The title compound (I-ah) (0.10 g) was a by product of the reaction described in Ex. 7 and was isolated as a white solid.

¹H-NMR (300 MHz, CD₃OD, ppm from TMS): 0.82 (3H, s); 0.98 (3H, s); 2.27–2.37 (1H, m); 3.16 (4H, m); 4.05 (1H, s); 6.30 (1H, dd); 6.58 (1H, dd); 7.00 (1H, d).

EXAMPLE 9

(E,E)-17β-{3-[3-(2-Dimethylaminoethyl)-guanidinoimino]-1-propenyl}-5β-androstane-3β,14β-diol (I-ai)

The title compound (I-ai) (0.90 g) was obtained as a white solid, starting from (E)-3β,14β-dihydroxy-5β-pregn-20-ene-21-carboxaldehyde (1.04 g) (Fullerton D. S. et al., *J. Med. Chem.*, 1976, 19, 1330) and 1-amino-3-(2-dimethylaminoethyl)guanidine hydroiodide (prepared following the procedure described in Houben-Weil, Metoden der Organischen Chemie, Band VIII, page 183) using the same procedure described in Ex. 1.

¹H-NMR (300 Mhz, CD₃OD, ppm from TMS): 0.88 (3H, s); 0.99 (3H, s); 2.25–2.35 (1H, m); 2.38 (6H, s); 2.70 (2H, t); 3.50 (2H, t); 4.05 (1H, s); 6.03 (1H, dd); 6.20 (1H, dd); 7.57 (1H, d).

EXAMPLE 10

(E,E)-17β-[3-(3-Phenyl)guanidinoimino-1-propenyl]-5β-androstane-3β,14β-diol (I-aj)

The title compound (I-aj) (0.85 g) was obtained as a white solid, starting from (E)-3β,14β-dihydroxy-5β-pregn-20-ene-21-carboxaldehyde (1.04 g) (Fullerton D. S. et al., *J. Med. Chem.*, 1976, 19, 1330) and 3-phenyl-1-aminoguanidine hydroiodide (prepared following the procedure described in Houben-Weil, Metoden der Organischen Chemie, Band VIII, page 183) using the same procedure described in Ex. 1.

¹H-NMR (300 MHz, CD₃OD, ppm from TMS): 0.93 (3H, s); 1.00 (3H, s); 2.20–2.25 (1H, m); 4.05 (1H, s); 5.98 (1H, dd); 6.22 (1H, dd); 6.70 (1H, m); 7.15 (2H, m); 7.35 (2H, m); 7.86 (1H, d).

EXAMPLE 11

(E,E)-17β-(3-Semicarbazono)-1-propenyl-5β-androstane-3β,14β-diol (I-ak)

The title compound (I-ak) (0.82 g) was obtained as a white solid, starting from (E)-3β,14β-dihydroxy-5β-pregn-20-ene-21-carboxaldehyde (1.04 g) (Fullerton D. S. et al., *J. Med. Chem.*, 1976, 19, 1330) and semicarbazide hydrochloride using the same procedure described in Ex. 1.

¹H-NMR (300 MHz, CDCl₃, ppm from TMS): 0.88 (3H, s); 0.95 (3H, s); 2.30–2.42 (1H, m); 4.13 (1H, s); 5.35 (2H, bb); 5.97 (1H, dd); 6.20 (1H, dd); 7.20 (1H, d); 7.80 (1H, s).

EXAMPLE 12

(E,E)-17β-(3-Thiosemicarbazono-1-propenyl)-5β-androstane-3β,14β-diol (I-al)

The title compound (I-al) (0.80 g) was obtained as a white solid, starting from (E)-3β,14β-dihydroxy-5β-pregn-20-ene-21-carboxaldehyde (1.04 g) (Fullerton D. S. et al., *J. Med. Chem.*, 1976, 19, 1330) and thiosemicarbazide using the same procedure described in Ex. 1.

¹H-NMR (300 MHz, CD₃OD, ppm from TMS): 0.89 (3H, s); 0.98 (3H, s); 2.20–2.25 (1H, m); 4.05 (1H, s); 5.97 (1H, dd); 6.17 (1H, dd); 7.75 (1H, d).

EXAMPLE 13

(E,E)-17β-(3-Hydroxyimino-1-propenyl)-5β-androstane-3β,14β-diol (I-am)

To a solution of 0.65 g of hydroxylamine hydrochloride in 41 ml of 1N NaOH and 30 ml of dioxane a solution of 2.70 g of (E)-3β,14β-dihydroxy-5β-pregn-20-ene-21-carboxaldehyde (Fullerton D. S. et al., *J. Med. Chem.*, 1976, 19,1330) in 40 ml of dioxane was added dropwise at room temperature. After 20 hrs the solution was diluted with water and extracted with methylene chloride. The crude product was purified by flash chromatography (SiO₂) using hexane/ethyl acetate 1/1 as the eluant. The fractions containing the title compound were collected and evaporated to dryness. The residue was ground with di-iso-propyl ether to give 1.80 g of the title compound (I-am), as a white solid.

¹H-NMR (300 MHz, CDCl₃, ppm from TMS): 0.83 (3H, s); 0.87 (3H, s); 2.38–2.47 (1H, m); 4.15 (1H, s); 5.90 (1H, dd); 6.33 (1H, dd); 7.50 (1H, d).

EXAMPLE 14

(E,E)-17β-(3-Methoxyimino-1-propenyl)-5β-androstane-3β,14β-diol (I-an)

The title compound (I-an) (0.64 g) was obtained as a white solid, starting from (E)-3β,14β-dihydroxy-5β-pregn-20-ene-21-carboxaldehyde (1.35 g) (Fullerton D. S. et al., *J. Med. Chem.*, 1976, 19, 1330) and methoxylamine hydrochloride using the same procedure described in Ex. 13.

¹H-NMR (300 MHz, CD₃OD, ppm from TMS): 0.84 (3H, s); 0.89 (3H, s); 2.35–2.45 (1H, m); 3.80 (3H, s); 4.13 (1H, s); 5.87 (1H, dd); 6.31 (1H, dd); 7.43 (1H, d).

EXAMPLE 15

(E,E)-17β-[3-(2-Aminoethoxyimino)-1-propenyl]-5β-androstane-3β,14β-diol (I-ao)

The title compound (I-ao) (0.92 g) was obtained as a white solid, starting from (E)-3β,14β-dihydroxy-5β-pregn-20-ene-21-carboxaldehyde (1.80 g) (Fullerton D. S. et al., *J. Med. Chem.*, 1976, 19, 1330) and 2-aminoethoxyamine dihydrochloride using the same procedure described in Ex. 13, but using chloroform/methanol/28% ammonium hydroxide 90/10/1 as the eluant.

$^1$H-NMR (300 MHz, CD$_3$OD, ppm from TMS): 0.85 (3H, s); 0.98 (3H, s); 2.23–2.34 (1H, m); 2.85 (2H, t); 4.00–4.20 (3H, m); 5.88 (1H, dd); 6.29 (1H, dd); 7.23 (1H, d).

EXAMPLE 16

(E,E)-17β-[3-(3-Aminopropoxyimino)-1-propenyl]-5β-androstane-3β,14β-diol (I-ap)

The title compound (I-ap) (0.95 g) was obtained as a white solid, starting from (E)-3β,14β-dihydroxy-5β-pregn-20-ene-21-carboxaldehyde (1.35 g) (Fullerton D. S. et al., *J. Med. Chem.*, 1976, 19, 1330) and 3-aminopropoxyamine dihydrochloride using the same procedure described in Ex. 13, but using chloroform/methanol/28% ammonium hydroxide 90/10/1 as the eluant.

$^1$H-NMR (300 MHz, CD$_3$OD, ppm from TMS): 0.86 (3H, s): 0.94 (3H, s); 2.25–2.35 (1H, m); 2.75 (2H, m); 4.05 (1H, s); 4.13 (2H, t); 5.89 (1H, dd); 6.30 (1H, dd); 7.73 (1H, d).

EXAMPLE 17

17β-[3-(EZ)-(2-Dimethylaminoethoxyimino)-1-(E)-propenyl]-5β-androstane-3β,14β-diol (I-aq)

The title compound (I-aq) (0.80 g) was obtained as a white solid, starting from (E)-3β,14β-dihydroxy-5β-pregn-20-ene-21-carboxaldehyde (1.35 g) (Fullerton D. S. et al, *JJ. Med. Chem.*, 1976, 19, 1330) and 2-dimethylaminoethoxyamine dihydrochloride using the same procedure described in Ex. 13, but using chloroform/methanol/28% ammonium hydroxide 90/10/1 as the eluant.

$^1$H-NMR (300 MHz, CD$_3$OD, ppm from TMS): 0.85 (3H, s); 0.95 (3H, s); 2.22–2.39 (1H, m); 2.32 (6H, s); 2.72 (2H, t); 4.05 (1H, s); 4.15 (2H, t); 5.88 (1H, dd); 6.22–6.35 (1H, m); 7.09 (0.1H, d); 7.71 (0.9H, d).

EXAMPLE 18

17β-[3-(3-(EZ)-Dimethylaminopropoxyimino)-1-(E)-propenyl]-5β-androstane-3β,14β-diol (I-ar)

The title compound (I-ar) (0.82 g) was obtained as a white solid, starting from (E)-3β,14β-dihydroxy-5β-pregn-20-ene-21-carboxaldehyde (1.35 g) (Fullerton D. S. et al., *J. Med. Chem.*, 1976, 19, 1330) and 3-dimethylaminopropoxyamine dihydrochloride using the same procedure described in Ex. 13, but using chloroform/methanol/28% ammonium hydroxide 90/10/1 as the eluant.

$^1$H-NMR (300 MHz, CD$_3$OD, ppm from TMS): 0.84 (3H, s); 0.92 (3H, s); 2.20–2.28 (1H, m); 2.30 (6H, s); 2.62 (2H, t); 4.05 (1H, s); 4.13 (2H, t); 5.89 (1H, dd); 6.15–6.30 (1H, m); 7.11 (0.1H, d); 7.70 (0.9H, d).

EXAMPLE 19

17β-[3-(EZ)-(2-Guanidinoethoxyimino)-1-(E)-propenyl]-5β-androstane-3β,14β-diol (I-as)

A solution of 1.00 g of (E,E)-17β-[3-(2-aminoethoxyimino)-1-propenyl]-5β-androstane-3β,14β-diol (I-ao) and 1.05 g of 1-amidino-3,5-dimethylpyrazole nitrate in 20 ml of ethanol was heated at reflux for 10 hrs. The solution was evaporated to dryness under reduced pressure and the crude product was ground with water and then with diethyl ether/ethanol to give 0.65 g of the title compound (I-as), as a nitrate, white solid.

$^1$H-NMR (300 MHz, CD$_3$OD, ppm from TMS): 0.85 (3H, s); 0.96 (3H, s); 2.23 (1H, m); 3.40 (2H, t); 4.05 (1H, s); 4.33 (2H, t); 5.90 (1H, dd); 6.23–6.37 (1H, m); 7.21 (0.1H, d); 7.82 (0.9H, d).

EXAMPLE 20

17β-[3-(EZ)-(3-Guanidinopropoxyimino)-1-(E)-propenyl]-5β-androstane-3β,14β-diol (I-at)

The title compound (I-at) (0.30 g) was obtained as a nitrate salt, white solid, starting from (E,E)-17β-[3-(3-aminopropoxyimino)-1-propenyl]-5β-androstane-3β,14β-diol (I-ap) (0.50 g) and 1-amidino-3,5-dimethylpyrazole nitrate using the procedure described in Ex. 19.

$^1$H-NMR (300 MHz, CD$_3$OD, ppm from TMS): 0.85 (3H, s); 0.96 (3H, s); 2.23 (1H, m); 3.42 (2H, t); 4.05 (1H, s); 4.25 (2H, t); 5.91 (1H, dd); 6.20–6.40 (1H, m); 7.09 (0.1H, d); 7.84 (0.9H, d).

EXAMPLE 21

(E,E,E)-17β-(5-Guanidinoimino)-1,3-pentadienyl)-5β-androstane-3β,14β-diol (I-au)

A mixture of 0.40 g of aminoguanidine hydrogencarbonate in 10 ml of water and 20 ml of dioxane was made acid to pH 3 with 1N HCl. A solution of 0.72 g of (E,E)-5-(3β,14β-dihydroxy-5β-androstane-17β-yl)-2,4-pentadienal (Prepn. 1) in 5 ml of dioxane was added at room temperature and left on standing for 13 days. The mixture was evaporated to dryness under reduced pressure. The crude product was crystallized from ethanol/water and then from ethanol to give 0.52 g of the title compound (I-au) as a white solid hydrochloride.

$^1$H-NMR (300 MHz, DMSO-d$_6$, ppm from TMS): 0.78 (3H, s); 0.88 (3H, s); 2.10–2.22 (1H, m); 3.85–3.97 (3H, m); 6.02 (1H, dd); 6.10–6.28 (2H, m); 6.75 (1H, dd); 7.43–7.72 (4H, bb); 7.80 (1H, d); 11.60 (1H, s).

EXAMPLE 22

(E,E,E)-17β-[5-(2-Imidazolin-2-yl)hydrazono-1,3-pentadienyl]-5β-androstane-3β,14β-diol (I-av)

The title compound (I-av) (0.25 g) was obtained as hydrobromide, white solid, starting from (E,E)-5-(3β,14β-dihydroxy-5β-androstane-17β-yl)-2,4-pentadienal (Prepn. 1) (0.36 g), 2-hydrazino-2-imidazoline hydrobromide and 0.1N HBr using the procedure described in Ex. 21.

$^1$H-NMR (300 MHz, DMSO-d$_6$, ppm from TMS): 0.78 (3H, s); 0.88 (3H, s); 2.12–2.25 (1H, m); 3.61 (4H, s); 3.86–3.96 (3H, m); 5.98 (1H, dd); 6.10–6.25 (2H, m); 6.76 (1H, dd); 7.81 (1H, d); 7.95–8.80 (2H, bb); 11.80 (1H, bb).

EXAMPLE 23

(E,E,E)-17β-[5-(1,4,5,6-Tetrahydro-2-pyrimidinyl)-hydrazono-1,3-pentadienyl]-5β-androstane-3β,14β-diol (I-aw)

The title compound (I-aw) (0.27 g) was obtained as a white solid, hydroiodide, starting from (E,E)-5-(3β,14β-dihydroxy-5β-androstane-17β-yl)-2,4-pentadienal (Prepn. 1) (0.36 g), 2-hydrazino-1,4,5,6-tetrahydro-2-pyrimidine hydroiodide and 0.1N HI using the procedure described in Ex. 21.

$^1$H-NMR (300 MHz, DMSO-d$_6$, ppm from TMS): 0.77 (3H, s); 0.89 (3H, s); 2.18–2.30 (1H, m); 3.60 (4H, s); 3.87–3.96 (3H, m); 6.00 (1H, dd); 6.12–6.28 (2H, m); 6.76 (1H, dd); 7.48–7.85 (2H, bb); 7.87 (1H, d); 11.80 (1H, bb).

EXAMPLE 24

(E,E,E)-17β-{5-[3-(2-Dimethylaminoethyl)-guanidinoimino]-1,3-pentadienyl}-5β-androstane-3β,14β-diol (I-ax)

The title compound (I-ax) (0.25 g) was obtained as hydroiodide, white solid, starting from (E,E)-5-(3β,14β-dihydroxy-5β-androstane-17β-yl)-2,4-pentadienal (Prepn. 1) (0.36 g), 1-amino-3-(2-dimethylaminoethyl)guanidine hydroiodide (prepared following the procedure described in Houben-Weil, Metoden der Organischen Chemie, Band VIII, page 183) and 0.1 N HI using the procedure described in Ex. 21.

$^1$H-NMR (300 MHz, DMSO-d$_6$, ppm from TMS): 0.80 (3H, s); 0.89 (3H, s); 2.10–2.25 (1H, m); 2.80 (6H, s); 3.15 (2H, m); 3.65 (2H, m); 3.88 (1H, m); 6.05 (1H, dd); 6.12–6.29 (2H, m); 6.76 (1H, dd); 7.68 (1H, d); 7.80–8.10 (3H, bb); 11.50 (1H, bb).

EXAMPLE 25

(E,E,E)-17β-(5-Semicarbazono-1,3-pentadienyl)-5β-androstane-3β,14β-diol (I-ay)

The title compound (I-ay) (0.27 g) was obtained as a white solid, starting from (E,E)-5-(3β,14β-dihydroxy-5β-androstane-17β-yl)-2,4-pentadienal (Prepn. 1) (0.36 g) and semicarbazide hydrochloride using the procedure described in Ex. 21. $^1$H-NMR (300 MHz, CDCl$_3$, ppm from TMS): 0.87 (3H, s); 0.94 (3H, s); 2.32–2.43 (1H, m); 4.13 (1H, s); 5.33 (2H, bb); 5.99 (1H, dd); 6.15–6.30 (2H, m); 6.70 (1H, dd); 7.18 (1H, d); 7.79 (1H, s).

EXAMPLE 26

(E,E,E)-17β-(5-Hydroxyimino-1,3-pentadienyl)-5β-androstane-3β,14β-diol (I-az)

The title compound (I-az) (0.22 g) was obtained as a white solid, starting from (E,E)-5-(3β,14β-dihydroxy-5β-androstane-17β-yl)-2,4-pentadienal (Prepn. 1) (0.36 g) and hydroxylamine hydrochloride using the procedure described in Ex. 21. $^1$H-NMR (300 MHz, CDCl$_3$, ppm from TMS): 0.80 (3H, s); 0.85 (3H, s); 2.39–2.48 (1H, m); 4.15 (1H, s); 5.95 (1H, dd); 6.20–6.32 (2H, m); 6.68 (1H, dd); 7.42 (1H, d).

EXAMPLE 27

(E,E,E)-17β-[5-(2-Aminoethoxyimino)-1,3-pentadienyl]-5β-androstane-3β,14β-diol (I-ba)

The title compound (I-ba) (0.32 g) was obtained as a white solid, base, starting from (E,E)-5-(3β,14β-dihydroxy-5β-androstane-17β-yl)-2,4-pentadienal (Prepn. 1) (0.36 g) and 2-aminoethoxyamine dihydrochloride using the procedure described in Ex. 21, but purifying the crude product by flash-chromatography (SiO$_2$) using chloroform/methanol/28% ammonium hydroxide 90/10/1 as the eluant.

$^1$H-NMR (300 MHz, MeOD, ppm from TMS): 0.83 (3H, s); 0.97 (3H, s); 2.24–2.36 (1H, m); 2.85 (2H, t); 4.05 (1H, s); 4.15 (2H, t); 5.90 (1H, dd); 6.25–6.33 (2H, m); 6.50 (1H, dd); 7.18 (1H, d).

EXAMPLE 28

(E,E,E)-17β-[5-(2-Dimethylaminoethoxyimino)-1,3-pentadienyl]-5β-androstane-3β,14β-diol (I-bb)

The title compound (I-bb) (0.25 g) was obtained as a white solid, base, starting from (E,E)-5-(3β,14β-dihydroxy-5β-androstane-17β-yl)-2,4-pentadienal (Prepn. 1) (0.36 g) and 2-dimethylaminoethoxyamine dihydrochloride using the procedure described in Ex. 27.

$^1$H-NMR (300 MHz, MeOD, ppm from TMS): 0.86 (3H, s); 0.97 (3H, s); 2.23–2.40 (1H, m); 2.32 (6H, s); 2.72 (2H, t); 4.05 (1H, s); 4.13 (2H, t); 5.92 (1H, dd); 6.25–6.33 (2h, m); 6.50 (1H, dd); 7.75 (1H, d).

EXAMPLE 29

(EZ)-17β-(2-Guaidinoimino)ethyl-5β-androstane-3β,14β-diol (I-bc)

A mixture of 0.15 g of aminoguanidine hydrogencarbonate in 10 ml of water and 20 ml of dioxane was made acid to pH 3 with 1N HCl. A solution of 0.67 g of 3β,14β-dihydroxy-5β-androstane-17β-ylacetaldehyde (Prepn. 2) in 5 ml of dioxane was added at room temperature. After 20 hrs the mixture was evaporated to dryness under reduced pressure. The crude product was purified by flash chromatography (SiO$_2$) using chloroform/methanol/28% ammonium hydroxide 80/20/3 as the eluant; the fractions containing the title compound were collected and evaporated to dryness. The residue was ground with diethyl ether and ethanol to give 0.50 g of the title compound (I-bc) as a white solid, base.

$^1$H-NMR (300 MHz, CD$_3$OD, ppm from TMS): 0.93 (3H, s); 0.98 (3H, s); 2.20–2.30 (1H, m); 4.05 (1H, s); 6.54 (0.1H, t); 7.24 (0.9 H, t).

EXAMPLE 30

(EZ)-17β-[2-(2-Imidazolin-2-yl)hydrazonoethyl]-5β-androstane-3β,14β-diol (I-bd)

The title compound (I-bd) (0.26 g) was obtained as a white solid, base, starting from 3β,14β-dihydroxy-5β-androstane-17β-ylacetaldehyde (Prepn. 2) (0.34 g) and 2-hydrazino-2-imidazoline hydrobromide using the procedure described in Ex. 29.

$^1$H-NMR (300 MHz, CD$_3$OD, ppm from TMS): 0.96 (3H, s); 0.98 (3H, s); 2.20–2.35 (1H, m); 3.48 (4H, s); 4.05 (1H, s); 6.67 (0.3H, t); 7.45 (0.7H, t).

EXAMPLE 31

(EZ)-17β-[2-(1,4,5,6-Tetrahydro-2-pyrimidinyl)-hydrazono-ethyl]-5β-androstane-3β,14β-diol (I-be)

The title compound (I-be) (0.24 g) was obtained as a white solid, base, starting from 3β,14β-dihydroxy-5β-androstane-17β-yl-acetaldehyde (Prepn. 2) (0.34 g) and 2-hydrazino-1,4,5,6-tetrahydro-2-pyrimidine hydroiodide using the procedure described in Ex. 29.

$^1$H-NMR (300 MHz, CD$_3$OD, ppm from TMS): 0.94 (3H, s); 0.97 (3H, s); 2.25–2.35 (1H, m); 3.12 (4H, m); 4.05 (1H, s); 6.69 (0.1H, t); 7.39 (0.9H, t).

EXAMPLE 32

(EZ)-17β-[2-(2-Aminoethoxyimino)ethyl]-5β-androstane-3β,14β-diol (I-bf)

To a solution of 0.47 g of 2-aminoethoxyamine hydrochloride in 16 ml of 1N NaOH and 20 ml of dioxane a solution of 0.89 g of 3β,14β-dihydroxy-5β-androstane-17β-ylacetaldehyde (Prepn. 2) in 15 ml of dioxane was added at room temperature. After 20 hrs the solution was extracted with ethyl acetate; the organic layer was dried over anhydrous sodium sulfate and evaporated to dryness. The crude product was purified by flash chromatography (SiO$_2$) using chloroform with increasing amounts of methanol (6 to 20%) as the eluant. The fractions containing the title compound were collected and evaporated to dryness. The residue was ground with di-iso-propyl ether to give 0.55 g of the title compound (I-bf), as a white foam.

$^1$H-NMR (300 MHz, CD$_3$OD, ppm from TMS): 0.95 (3H, s) 1.00 (3H, s); 2.23–2.34 (1H, m); 2.83 (2H, t); 4.05 (1H, s); 4.15 (2H, t); 6.69 (0.3H, t); 7.52 (0.7H, t).

EXAMPLE 33

(EZ)-17β-[2-(3-Aminopropoxyimino)ethyl]-5β-androstane-3β,14β-diol (I-bg)

The title compound (I-bg) (0.26 g) was obtained as a white foam, starting from 3β,14β-dihydroxy-5β-androstane-17β-ylacetaldehyde (Prepn. 2) (0.45 g) and 3-aminopropoxyamine dihydrochloride using the procedure described in Ex. 32.

$^1$H-NMR (300 MHz, CD$_3$OD, ppm from TMS): 0.97 (3H, s); 0.99 (3H, s); 2.25–2.35 (1H, m); 2.70 (2H, t); 4.05 (1H, s); 4.11 (2H, t); 6.48 (0.3H, t); 7.38 (0.7H, t).

EXAMPLE 34

(EZ)-17β-[2-(2-Dimethylaminoethoxyimino)ethyl]-5β-androstane-3β,14β-diol (I-bh)

The title compound (I-bh) (0.33 g) was obtained as white solid, oxalate, starting from 3β,14β-dihydroxy-5β-androstane-17β-ylacetaldehyde (Prepn. 2) (0.45 g) and 2-dimethylaminoethoxyamine dihydrochloride using the procedure described in Ex. 32, after salification of the free base with the stoichiometric amount of oxalic acid.

$^1$H-NMR (300 MHz, CD$_3$OD, ppm from TMS): 0.95 (3H, s); 0.97 (3H, s); 2.23–2.32 (1H, m); 2.92 (6H, s); 3.45–3.50 (2H, m); 4.05 (1H, s); 4.40–4.48 (2H, m); 6.96 (0.4H, t); 7.46 (0.6H, t).

EXAMPLE 35

(EZ)-17β-(3-Guanidinoiminopropyl)-5β-androstane-3β,14β-diol (I-bi)

The title compound (I-bi) (0.55 g) was obtained as a white solid, starting from 3-(3β,14β-dihydroxy-5β-androstane-17β-yl)propionaldehyde (Prepn. 3) (0.70 g) and aminoguanidine hydrogencarbonate using the procedure described in Ex. 29.

$^1$H-NMR (300 MHz, CD$_3$OD, ppm from TMS): 0.94 (3H, s); 0.97 (3H, s); 2.21–2.32 (1H, m); 4.05 (1H, s); 6.60 (0.1H, t); 7.30 (0.9 H, t).

EXAMPLE 36

(EZ)-17β-[3-(2-Imidazolin-2-yl)hydrazonopropyl]-5β-androstane-3β,14β-diol (I-bj)

The title compound (I-bj) (0.30 g) was obtained as a white solid, starting from 3-(3β,14β-dihydroxy-5β-androstane-17β-yl)propionaldehyde (Prepn. 3) (0.35 g) and 2-hydrazino-2-imidazoline hydrobraomide using the procedure described in Ex. 29.

$^1$H-NMR (300 MHz, CD$_3$OD, ppm from TMS): 0.94 (3H, s); 0.99 (3H, s); 2.20–2.34 (1H, m); 3.49 (4H, s); 4.05 (1H, s); 6.78 (0.1H, t); 7.48 (0.9H, t).

EXAMPLE 37

(EZ)-17β-[3-(1-Methyl-2-imidazolin-2-yl)-hydrazonopropyl]-5β-androstane-3β,14β-diol (I-bk)

The title compound (I-bk) (0.28 g) was obtained as a white solid, starting from (3-(3β,14β-dihydroxy-5β-androstane-17β-yl)-propionaldehyde (Prepn. 3) (0.35 g) and 1-methyl-2-hydrazinoimidazoline hydroiodide (prepared from 2-methylthio-1-methylimidazoline hydroiodide and hydrazine following the procedure described in Houben-Weil, Metoden der Organischen Chemie, Band VIII, page 183) using the procedure described in Ex. 29.

$^1$H-NMR (300 MHz, CD$_3$OD, ppm from TMS): 0.97 (3H, s); 0.99 (3H, s); 2.20–2.35 (1H, m); 3.00 (3H, s); 3.48 (4H, s); 4.05 (1H, m); 6.76 (0.1H, t); 7.46 (0.9H, t).

EXAMPLE 38

(EZ)-17β-[3-(1,4,3,6-Tetrahydro-2-pyrimidinyl)-hydrazono-propyl]-5β-androstane-3β,14β-diol (I-bl)

The title compound (I-bl) (0.45 g) was obtained as a white solid, starting from 3-(3β,14β-dihydroxy-5β-androstane-17β-yl)propionaldehyde (Prepn. 3) (0.35 g) and 2-hydrazino-1,4,5,6-tetrahydro-2-pyrimidine hydroiodide (prepared from 2-methylthio-1,4,5,6-tetrahydro-2-pyrimidine hydroiodide and hydrazine following the procedure described in Houben-Weil, Metoden der Organischen Chemie, Band VIII, page 183) using the procedure described in Ex. 29.

$^1$H-NMR (300 MHz, CD$_3$OD, ppm from TMS): 0.93 (3H, s); 0.98 (3H, s); 2.21–2.33 (1H, m); 3.14 (4H, s); 4.05 (1H, m); 6.71 (0.1H, t); 7.41 (0.9H, t).

EXAMPLE 39

(EZ)-17β-[3-(2-Aminoethoxyimino)propyl]-5β-androstane-3β,14β-diol (I-bm)

The title compound (I-bm) (0.25 g) was obtained as a white foam, starting from 3-(3β,14β-dihydroxy-5β-androstane-17β-yl)propionaldehyde (Prepn. 3) (0.92 g) and 2-aminoethoxyamine hydrochloride using the procedure described in Ex. 32.

$^1$H-NMR (300 MHz, CD$_3$OD, ppm from TMS): 0.94 (3H, s); 0.98 (3H, s); 2.19–2.33 (1H, m); 2.82 (2H, t); 4.05 (1H, s); 4.13 (2H, t); 6.38 (0.3H, t); 7.25 (0.7H, t).

EXAMPLE 40

(EZ)-17β-[3-(2-Dimethylaminoethoxyimino)propyl]-5β-androstane-3β,14β-diol (I-bn)

The title compound (I-bn) (0.30 g) was obtained as white solid, oxalate, starting from of 3-(3β,14β-dihydroxy-5β-androstane-17β-yl)propionaldehyde (Prepn. 3) (0.45 g) and 2-dimethylaminoethoxyamine dihydrochloride using the procedure described in Ex. 32, after salification of the free base with the stoichiometric amount of oxalic acid.

$^1$H-NMR (300 MHz, CD$_3$OD, ppm from TMS): 0.93 (3H, s); 0.98 (3H, s); 2.15–2.30 (1H, m); 2.92 (6H, s); 3.45–3.49 (2H, m); 4.05 (1H, s); 4.30–4.38 (2H, m); 6.81 (0.4H, t); 7.49 (0.6H, t).

EXAMPLE 41

(E,E)-17β-(3-Guanidinoimino-1-propenyl)-5β-androstane-3β,14β,17α-triol (I-bo)

The title compound (I-bo) (0.33 g) was obtained as a white solid, base, starting from (E)-3β,14β,17α-trihydroxy-5β-pregn-20-ene-21-carboxaldehyde (Prepn. 4) (0.54 g) and aminoguanidine hydrogencarbonate using the procedure described in Ex. 1.

$^1$H-NMR (300 MHz, CD$_3$OD, ppm from TMS): 0.82 (3H, s); 0.97 (3H, s); 4.05 (1H, s); 6.00 (1H, dd); 6.50 (1H, dd); 7.65 (1H, d).

EXAMPLE 42

(E,E)-17β-[3-(2-Imidazolin-2-yl)hydrazono-1-propenyl]-5β-androstane-3β,14β,17α-triol (I-bp)

The title compound (I-bp) (0.35 g) was obtained as a white solid, base, starting from (E)-3β,14β,17α-trihydroxy-5β-pregn-20-ene-21-carboxaldehyde (Prepn. 4) (0.54 g) and 2-hydrazino-2-imidazoline hydrobromide using the procedure described in Ex. 3.

$^1$H-NMR (300 MHz, CD$_3$OD, ppm from TMS): 0.79 (3H, s); 0.95 (3H, s); 3.51 (4H, s); 4.05 (1H, s); 6.10 (1H, dd); 6.30 (1H, dd); 7.64 (1H, d).

EXAMPLE 43

(E,E)-17β-[3-(2-Dimethylaminoethoxyimino)-1-propenyl]-5β-androstane-3β,14β-17α-triol (I-bq)

The title compund (I-bq) (0.32 g) was obtained as a white solid, starting from (E)-3β,14β,17α-trihydroxy-5β-pregn-20-ene-21-carboxaldehyde (Prepn. 4) (0.54 g) and 2-dimethylaminoethoxyamine dihydrochloride using the same procedure described in Ex. 13, but using chloroform/methanol/28% ammonium hydroxide 90/10/1 as the eluant.

$^1$H-NMR (300 MHz, CD$_3$OD, ppm from TMS): 0.81 (3H, s); 0.92 (3H, s); 2.28 (6H, s); 2.62 (2H, m); 4.05 (1H, s); 4.12 (2H, m); 6.24 (1H, dd); 6.80 (1H, dd); 7.76 (1H, d).

EXAMPLE 44

(E,E,E)-17β-(5-Guanidinoimino-1,3-pentadienyl)-5β-androstane-3β,14β,17α-triol (I-br)

The title compound (I-br) (0.40 g) was obtained as a white solid, starting from (E,E)-5-(3β,14β,17α-trihydroxy-5β-androstane-17β-yl)-2,4-pentadienal (Prepn. 5) (0.75 g) and aminoguanidine hydrogencarbonate using the procedure described in Ex. 21.

$^1$H-NMR (300 MHz, CD$_3$OD, ppm from TMS): 0.84 (3H, s); 0.98 (3H, s); 4.05 (1H, s); 6.00 (1H, dd); 6.20–6.32 (2H, m); 6.73 (1H, dd); 7.77 (1H, d).

EXAMPLE 45

(EZ)-17β-(2-Guanidinoimino)ethyl-5β-androstane-3β,14β,17α-triol (I-bs)

The title compound (I-bs) (0.38 g) was obtained as a white solid, starting from 3β,14β,17α-trihydroxy-5β-androstane-17β-ylacetaldehyde (Prepn. 6) (0.70 g) and aminoguanidine hydrogencarbonate using the procedure described in Ex. 29.

$^1$H-NMR (300 MHz, CD$_3$OD, ppm from TMS): 0.95 (3H, s); 0.99 (3H, s); 4.05 (1H, s); 6.94 (0.1H, t); 7.60 (0.9 H, t).

EXAMPLE 46

(EZ)-17β-[2-(2-Dimethylaminoethoxyimino)ethyl]-5β-androstane-3β,14β,17α-triol (I-bt)

The title compound (I-bt) (0.20 g) was obtained as white solid, starting from 3β,14β,17α-trihydroxy-5β-androstane-17β-ylacetaldehyde (Prepn. 6) (0.35 g) and 2-dimethylaminoethoxyamine dihydrochloride using the procedure described in Ex. 32, but carrying out the reaction for 20 hrs and using chloroform/methanol/28% ammonium hydroxide 90/10/1 as the eluant.

$^1$H-NMR (300 MHz, CD$_3$OD, ppm from TMS): 0.96 (3H, s); 1.00 (3H, s); 2.32 (6H, s); 3.45–3.50 (2H, m); 4.05 (1H, s); 4.40–4.48 (2H, m); 6.96 (0.4H, t); 7.46 (0.6H, t).

EXAMPLE 47

(EZ)-17β-(3-Guanidinoimino)ethyl-5β-androstane-3β,14β,17α-triol (I-bu)

The title compound (I-bu) (0.50 g) was obtained as a white solid, starting from 3-(3β,14β,17α-trihydroxy-5β-androstane-17β-yl)propionaldehyde (Prepn. 7) (0.70 g) and aminoguanidine hydrogencarbonate using the procedure described in Ex. 29.

$^1$H-NMR (300 MHz, CD$_3$OD, ppm from TMS): 0.93 (3H, s); 0.97 (3H, s); 4.05 (1H, s); 6.98 (0.1H, t); 7.63 (0.9 H, t).

EXAMPLE 48

(EZ)-17β-[3-(2-Dimethylaminoethoxyimino)propyl]-5β-androstane-3β,14β,17α-triol (I-bw)

The title compound (I-bw) (0.20 g) was obtained as oxalate, white solid, starting from of 3-(3β,14β,17α-trihydroxy-5β-androstane-17β-yl)propionaldehyde (Prepn. 7) (0.36 g) and 2-dimethylaminoethoxyamine dihydrochloride using the procedure described in Ex. 32. The free base was then salified with the stoichiometric amount of oxalic acid.

¹H-NMR (300 MHz, CD₃OD, ppm from TMS): 0.96 (3H, s); 1.00 (3H, s); 2.92–2.94 (6H, 2s); 3.40–3.50 (2H, m); 4.05 (1H, s); 4.28–4.38 (2H, m); 6.80 (0.4H, t); 7.50 (0.6H, t).

EXAMPLE 49

3β-[2-(1-Pyrrolidinyl)ethoxy]-17β-(3-(E,Z)-guanidinoimino-1-(E)-propenyl)-5β-androstane-3β,14β-diol (I-bx)

A solution of 0.53 g (E)-3β-[2-(1-pyrrolidinyl)ethoxy]-21-[2-(1,3-dioxolanyl)]-5β-pregn-20-ene-14β-ol (Prepn. 8) and 15 ml of 0.1M hydrochloric acid in 40 ml of dioxane was kept at room temperature. After 1 day 0.15 g of aminoguanidine hydrogencarbonate were added. After 2 days the solution was evaporated to dryness under reduced pressure. The crude product was purified by flash-chromatography (SiO₂) using chloroform/methanol/28% ammonium hydroxide 80/20/3 as the eluant; the fractions containing the title compound were collected and evaporated to dryness. The free base was then salified with the stoichiometric amount of oxalic acid to give 0.32 g of the title compound (I-bx) as a white solid.

¹H-NMR (300 MHz, CD₃OD, ppm from TMS): 0.92 (3H, s); 1.05 (3H, s); 2.40–2.52 (1H, m); 3.20–3.50 (6H, m); 3.65–3.82 (3H, s); 5.98 (0.9H, dd); 6.18 (0.9H, dd); 6.32 (0.1H, dd); 6.61 (0.1H, dd); 7.10 (0.1H, d); 7.62 (0.9H, d).

EXAMPLE 50

3β-[2-(1-Pyrrolidinyl)ethoxy]-17β-[3-(EZ)-(2-dimethylamino-ethoxyimino)-1-(E)-propenyl]-5β-androstane-14β-ol (I-by)

The title compound (I-by) (0.34 g) was obtained as a white solid, starting from (E)-3β-[2-(1-pyrrolidinyl)ethoxy]-21-[2-(1,3-dioxalanyl)]-5β-pregn-20-ene-14β-ol (Prepn. 8) (0.53 g) and 2-dimethylaminoethoxyamine dihydrochloride using the same procedure described in Ex. 49, but using chloroform/methanol/28% ammonium hydroxide 90/10/1 as the eluant.

¹H-NMR (300 MHz, CD₃OD, ppm from TMS): 0.84 (3H, s); 0.95 (3H, s); 2.20–2.38 (7H, m); 2.50–2.65 (4H, m); 2.70 (2H, t); 2.80 (2H, t); 3.55 (2H, m); 3.65 (1H, m); 4.10 (2H, t); 5.89 (0.9H, dd); 6.20–6.40 (1.1H, m); 7.10 (0.1H, d); 7.72 (0.9H, d).

EXAMPLE 51

3β-[2-(1-Pyrrolidinyl)propoxy]-17β-[(EZ)-3-guanidinoimino-1-(E)-propenyl]-5β-androstane-3β,14β-diol (I-bz)

The title compound (I-bz) (0.41 g) was obtained as a white solid, oxalate, starting from (E)-3β-[2-(1-pyrrolidinyl)propoxy]-21-[2-(1,3-dioxolanyl)]-5β-pregn-20-ene-14β-ol (Prepn. 9) (0.54 g) and aminoguanidine hydrogencarbonate using the same procedure described in Ex. 49.

¹H-NMR (300 MHz, CD₃OD, ppm from TMS): 0.91 (3H, s); a1.03 (3H, s); 2.39–2.55 (1H, m); 3.20–3.56 (6H, m); 3.65–3.85 (3H, s); 5.96 (0.9H, dd); 6.19 (0.9H, dd); 6.30 (0.1H, dd); 6.63 (0.1H, dd); 7.10 (0.1H, d); 7.62 (0.9H, d).

EXAMPLE 52

3β-[2-(1-Pyrrolidinyl)propoxy]-17β-[3-(EZ)-(2-dimethylamino-ethoxyimino)-1-(E)-propenyl]-5β-androstane-14β-ol (I-ca)

The title compound (I-ca) (0.13 g) was obtained as a white solid, starting from (E)-3β-[2-(1-pyrrolidinyl)propoxy]-21-[2-(1,3-dioxolanyl)]-5β-pregn-20ene-14β-ol (Prepn. 9) (0.54 g) and 2-dimethylaminoethoxyamine dihydrochloride using the same procedure described in Ex. 49.

¹H-NMR (300 MHz, CD₃OD, ppm from TMS): 0.84 (3H, s); 0.95 (3H, s); 2.20–2.38 (7H, m); 2.42–2.58 (4H, m); 2.73 (2H, t); 2.80 (2H, t); 3.55 (2H, m); 3.65 (1H, m); 4.10 (2H, t); 5.90 (0.9H, dd); 6.20–6.42 (1.1H, m); 7.12 (0.1H, d); 7.71 (0.9H, d).

EXAMPLE 53

(3β-(2-Aminoethoxy)-17β-(3-(EZ)-guanidinoimino-1-(E)-propenyl)-5β-androstane-3β,14β-diol (I-cb)

The title compound (I-cb) (0.18 g) was obtained as dioxalate, white solid, starting from (E)-3β-(3-aminoethoxy)-21-[2-(1,3-dioxolanyl)]-5β-pregn-20-ene-14β-ol (Prepn. 10) (0.47 g) and aminoguanidine hydrogencarbonate using the same procedure described in Ex. 49.

¹H-NMR (300 MHz, CD₃OD, ppm from TMS): 0.92 (3H, s); 0.98 (3H, s); 2.40–2.52 (1H, m); 3.08 (2H, t); 3.55 (2H, t); 3.80 (1H, s); 6.00 (0.9H, dd); 6.17 (0.9H, dd); 6.30 (0.1H, dd); 6.63 (0.1H, dd); 7.10 (0.1H, d); 7.62 (0.9H, d).

EXAMPLE 54

3β-(2-Aminoethoxy)-17β-[3-(EZ)-(2-dimethylaminoethoxyimino)-1-(E)-propenyl]-5_62-androstane-14β-ol (I-cc)

The title compound (I-cc) (0.34 g) was obtained as a white solid, starting from (E)-3β-(2-Aminoethoxy)-21-[2-(1,3-dioxolanyl)]-5β-pregn-20-ene-14β-ol (Prepn. 10) (0.47 g) and 2-dimethylaminoethoxyamine dihydrochloride using the same procedure described in Ex. 49.

¹H-NMR (300 MHz, CD₃OD, ppm from TMS): 0.85 (3H, s); 0.95 (3H, s); 2.12–2.39 (7H, m); 2.65 (2H, t); 2.80 (2H, t); 3.50 (2H, t); 3.62 (1H, s); 4.10 (2H, t); 5.88 (0.9H, dd); 6.20–6.41 (1.1H, m); 7.13 (0.1H, d); 7.72 (0.9H, d).

EXAMPLE 55

(E,E)-3β-(3-Aminopropoxy)-17β-(3-guanidinoimino-1-propenyl)-5β-androstane-3β,14β-diol (I-cd)

The title compound (I-cb) (0.27 g) was obtained as dioxalate, white solid, starting from (E)-3β-(3-aminopropoxy)-21-[2-(1,3-dioxolanyl)]-5β-pregn-20-ene-14β-ol (Prepn. 11) (0.48 g) and aminoguanidine hydrogencarbonate using the same procedure described in Ex. 49. The free base was then salified with the stoichiometric amount of oxalic acid.

¹H-NMR (300 MHz, CD₃OD, ppm from TMS): 0.86 (3H, s); 0.95 (3H, s); 2.40–2.58 (1H, m); 3.09 (2H, t); 3.60 (1H, s); 3.78 (1H, t); 5.98 (1H, dd); 6.20 (1H, dd); 7.66 (1H, d).

EXAMPLE 56

3β-(3-Aminopropoxy)-17β-[3-(EZ)-(2-dimethylamino-ethoxy-imino)-1-(E)-propenyl]-5β-androstane-14β-ol (I-ce)

The title compound (I-ce) (0.13 g) was obtained as a white solid, starting from (E)-3β-(2-aminopropoxy)-21-[2-(1,3-dioxolanyl)]-5β-pregn-20-ene-14β-ol (Prepn. 11) (0.48 g) and 2-dimethylaminoethoxyamine dihydrochloride using the same procedure described in Ex. 49.

$^1$H-NMR (300 MHz, CD$_3$OD, ppm from TMS): 0.84 (3H, s); 0.95 (3H, s); 2.12–2.40 (7H, m); 2.60 (2H, t); 2.78 (2H, t); 3.47 (2H, t); 3.61 (1H, s); 4.05–4.20 (2H, m); 5.89 (0.6H, dd); 6.18–6.38 (1.4H, m); 7.10 (0.4H, d); 7.73 (0.6H, d).

EXAMPLE 57

(EZ)-3β-[2-(1-Pyrrolidinyl)ethoxy]-17β-(2-guanidinoimino)-ethyl-5β-androstane-3β,14β-diol (I-cf)

The title compound (I-cf) (0.31 g) was obtained as a white solid, starting from (E)-3β-[2-(1-pyrrolidinyl)ethoxy]-17β-[2-(1,3-dioxolanyl)]methyl-5β-androstane-14β-ol (Prepn. 12) (0.47 g) and aminoguanidine hydrogencarbonate using the same procedure described in Ex. 49.

$^1$H-NMR (300 MHz, CD$_3$OD, ppm from TMS): 0.92 (3H, s); 0.97 (3H, s); 2.22–2.32 (1H, m); 2.40–2.58 (4H, m); 2.70 (2H, t); 3.55 (2H, m); 3.65 (1H, m); 6.80 (0.1H, t); 7.40 (0.9H, t).

EXAMPLE 58

3β-[2-(1-Pyrrolidinyl)ethoxy]-17β-[3-(EZ)-(2-dimethylamino-ethoxyimino)ethyl]-5β-androstane-14β-ol (I-cg)

The title compound (I-cg) (0.34 g) was obtained as a white solid, starting from (E)-3β-[2-(1-pyrrolidinyl)ethoxy]-17β-[2-(1,3-dioxolanyl)]methyl-5β-androstane-14β-ol (Prepn. 12) (0.47 g) and 2-dimethylaminoethoxyamine dihydrochloride using the same procedure described in Ex. 49.

$^1$H-NMR (300 MHz, CD$_3$OD, ppm from TMS): 0.94 (3H, s); 0.98 (3H, s); 2.20–2.35 (7H, m); 2.40–2.58 (4H, m); 2.65–2.73 (2H, m); 2.82 (2H, t); 3.55 (2H, m); 3.60–3.72 (1H, m); 4.10 (2H, t); 6.80 (0.4H, d); 7.40 (0.6H, d).

EXAMPLE 59

(EZ)-3β-[3-(1-Pyrrolidinyl)propoxy]-17β-(2-guanidinoimino)-ethyl-5β-androstane-3β,14β-diol (I-ch)

The title compound (I-ch) (0.31 g) was obtained as a white solid, starting from (E)-3β-[3-(1-pyrrolidinyl)propoxy]-17β-[2-(1,3-dioxolanyl)]methyl-5β-androstane-14β-ol (Prepn. 13) (0.48 g) and aminoguanidine hydrogencarbonate using the same procedure described in Ex. 49.

$^1$H-NMR (300 MHz, CD$_3$OD, ppm from TMS): 0.93 (3H, s); 0.98 (3H, s); 2.22–2.35 (1H, m); 2.38–2.59 (4H, m); 2.70 (2H, t); 3.55 (2H, m); 3.68 (1H, m); 6.81 (0.1H, t); 7.42 (0.9H, t).

EXAMPLE 60

3β-[3-(1-Pyrrolidinyl)propoxy]-17β-[3-(EZ)-(2-dimethylamino-ethoxyimino)ethyl]-5β-androstane-14β-ol (I-ci)

The title compound (I-ci) (0.34 g) was obtained as a white solid, starting from ((E)-3β-[3-(1-pyrrolidinyl)propoxy]-17β-[2-(1,3-dioxolanyl)]methyl-5β-androstane-14β-ol (Prepn. 13) (0.48 g) and 2-dimethylaminoethoxyamine dihydrochloride using the same procedure described in Ex. 50.

$^1$H-NMR (300 MHz, CD$_3$OD, ppm from TMS): 0.94 (3H, s); 0.98 (3H, s); 2.20–2.35 (7H, m); 2.36–2.56 (4H, m); 2.65–2.85 (4H, m); 3.53–3.60 (2H, m); 3.65 (1H, m); 4.10 (2H, t); 6.78 (0.4H, d); 7.39 (0.6H, d).

EXAMPLE 61

(E,E)-17β-(3-Guanidinoimino-1-propenyl)-5β-androstane-3α,14β-diol (I-cj)

The title compound (I-cj) (0.30 g) was obtained as a white solid starting from (E)-3α,14β-dihydroxy-5β-pregn-20-ene-21-carboxaldehyde (Prepn. 14) (0.41 g) and aminoguanidine hydrogencarbonate using the same procedure described in Ex. 1.

$^1$H-NMR (300 MHz, CD$_3$OD, ppm from TMS): 0.83 (3H, s); 0.95 (3H, s); 2.20–2.34 (1H, m); 3.68 (1H, s); 5.97 (1H, dd); 6.18 (1H, dd); 7.62 (1H, d).

EXAMPLE 62

(E,E)-17β-[3-(2-Dimethylaminoethoxyimino)-1-propenyl]-5β-androstane-3α,14β-diol (I-ck)

The title compound (I-ck) (0.32 g) was obtained as a white solid, starting from (E)-3α,14β-dihydroxy-5β-pregn-20-ene-21-carboxaldehyde (Prepn. 14) (0.41 g) and 2-dimethylaminoethoxyamine dihydrochloride using the same procedure described in Ex. 13, but using chloroform/methanol/28% ammonium hydroxide 90/10/1 as the eluant.

$^1$H-NMR (300 MHz, CD$_3$OD, ppm from TMS): 0.86 (3H, s); 0.97 (3H, s); 2.23–2.40 (1H, m); 2.32 (6H, s); 2.74 (2H, t); 3.68 (1H, s); 4.13 (2H, t); 5.88 (0.9H, dd); 6.22–6.35 (1.1H, m); 7.09 (0.1H, d); 7.71 (0.9H, d).

EXAMPLE 63

(EZ)-17β-(2-Guanidinoimino)ethyl-5β-androstane-3α,14β-diol (I-cl)

The title compound (I-cl) (0.32 g) was obtained as a white solid starting from 3α,14β-dihydroxy-5β-androstane-17β-ylacetaldehyde (Prepn. 15) (0.67 g) and aminoguanidine hydrogencarbonate using the same procedure described in Ex. 29

$^1$H-NMR (300 MHz, CD$_3$OD, ppm from TMS): 0.94 (3H, s); 0.99 (3H, s); 2.20–2.34 (1H, m); 3.68 (1H, s); 6.52 (0.1H, t); 7.23 (0.9H, t).

EXAMPLE 64

(EZ)-17β-[2-(2-Dimethylaminoethoxyimino)ethyl]-5β-androstane-3α,14β-diol (I-cm)

The title compound (I-cm) (0.24 g) was obtained as a white solid, oxalate, starting from 3α,14β-dihydroxy-5β-androstane-17β-ylacetaldehyde (Prepn. 15) (0.45 g) and 2-dimethylaminoethoxyamine dihydrochloride using the procedure described in Ex. 32, after salification of the free base witht he stoichiometric amount of oxalic acid.

$^1$H-NMR (300 MHz, CD$_3$OD, ppm from TMS): 0.93 (3H, s); 0.98 (3H, s); 2.20–2.35 (1H, m); 2.92 (6H, s); 3.43–3.52 (2H, m); 3.68 (1H, s); 4.41–4.47 (2H, m); 6.96 (0.4H, t); 7.47 (0.6H, t).

PREPARATION 1

(E,E)-5-(3β,14β-Dihydroxy-5β-androstane-17β-yl)-2,4-penta-dienal (II-a)

To a solution of 7.95 g of methyl (E,E)-5-(3β,14β-dihydroxy-5β-androstane-17β-yl)-2,4-pentadienoate (Boutagy J. and Thomas R., *Aust. J. Pharm. Chem.*, 1972, NS1, 67) in 390 ml of dry tetrahydrofuran, 133 ml of 1M i-Bu$_2$AlH in hexane were added dropwise under nitrogen at −78° C. After 2 hrs the reaction was quenched with aqueous sodium sulfate (63 g in 390 ml of water) and stirred at room temperature overnight. The mixture was then filtered through Celite and washed with ethyl acetate. The organic solution was dried over anhydrous sodium sulfate and evaporated to dryness to give 4.90 g of (E,E)-5-(3β,14β-dihydroxy-5β-androstane-17β-yl)-2,4-pentadien-1-ol as an off-white solid.

$^1$H-NMR (300 MHz, CDCl$_3$, ppm from TMS): 0.70 (3H, s); 0.85 (3H, s); 2.05–2.15 (1H, m); 3.99 (2H, s); 4.05 (1H, m); 5.55–5.65 (1H, m); 5.69–5.85 (2H, m); 6.05–6.15 (1H, m).

To a solution of 4.90 g of (E,E)-5-(3β,14β-dihydroxy-5β-androstane-17β-yl)-2,4-pentadien-1-ol in 160 ml of chloroform and 40 ml of iso-propanol, 10.40 g of MnO$_2$ were added at room temperature. The mixture was stirred overnight and then filtered through Celite. The organic solution was evaporated to dryness to give 4.80 g of the title compound (II-a) as an off-white solid.

$^1$H-NMR (300 MHz, DMSO-d$_6$, ppm from TMS): 0.73 (3H, s); 0.89 (3H, s); 2.19–2.30 (1H, m); 3.88 (1H, s); 3.92 (1H, s); 4.18 (1H, s); 6.02 (1H, dd); 6.14 (1H, dd); 6.55 (1H, dd); 7.31 (1H, dd); 9.49 (1H, d).

PREPARATION 2

3β,14β-Dihydroxy-5β-androstane-17β-ylacetaldehyde (II-b)

To a solution of 13.86 g of 3β-acetoxy-21-nitro-5β-pregn-20-en-14β-ol (Eberlein W. et al., *Chem. Ber.*, 1974, 107, 1275) in 440 ml of diethyl ether and 440 ml of ethanol, 2.86 g NaBH$_4$ were added at room temperature. After 1 hr. the mixture was neutralized with aqueous sodium dihydrogenphosphate and extracted with methylene chloride. The organic layer was washed with water, dried over anhydrous sodium sulfate and evaporated to dryness to give 13.40 g of 3β-acetoxy-21-nitro-5β-pregnane-14β-ol.

$^1$H-NMR (300 MHz, CDCl$_3$, ppm from TMS): 1.00 (6H, as); 2.07 (3H, s); 2.28–2.45 (1H, m); 4.29–4.49 (2H, m); 5.09 (1H, s).

A solution of 13.34 g of 3β-acetoxy-21-nitro-5β-pregnane-14β-ol and 39.1 g of triphenylphosphine in 370 ml of dry methylene chloride was kept at 0° C. under nitrogen; 19.3 ml of diethyl azodicarboxylate were added dropwise during 1 hr. After 2 hrs. the solvent was removed in vacuo and the crude product was purified by flash-chromatography (SiO$_2$) using methylene chloride/diethyl ether 95/5 as the eluant to give 11.20 g of 3β-acetoxy-14β-hydroxy-5β-pregnane-21-nitrile.

$^1$H-NMR (300 MHz, CDCl$_3$, ppm from TMS): 0.92 (6H, s); 1.99 (3H, s); 2.06–2.15 (1H, m); 2.40–2.62 (2H, m); 5.09 (1H, s).

A solution of 11.18 g of 3β-acetoxy-14β-hydroxy-5β-pregnane-21-nitrile in 260 ml of methanol, 260 ml of tetrahydrofuran and 143 ml of 1N NaOH was stirred at room temperature for 20 hrs. The mixture was then neutralized with sodium dihydrogenphosphate and extracted with ethyl acetate. The organic layer was dried over anhydrous sodium sulfate and the solvent was evaporated to dryness under reduced pressure to give 8.55 g of 3β,14β-dihydroxy-5β-pregnane-21-nitrile.

$^1$H-NMR (300 MHz, CDCl$_3$, ppm from TMS): 0.94 (6H, s); 2.10–2.29 (1H, m); 2.46–2.70 (2H, m); 4.12 (1H, s).

To a solution of 8.50 g of 3β,14β-dihydroxy-5β-pregnane-21-nitrile in 500 ml of dry tetrahydrofuran, 105 ml of 1M i-Bu$_2$AlH in hexane were added dropwise under nitrogen at 0° C. After 1 hr the reaction was quenched with aqueous citric acid (7.05 g in 32.5 ml of water) and stirred at room temperature for 1 hr. The mixture was then filtered through Celite and washed with ethyl acetate. The organic solution was dried over anhydrous sodium sulfate and evaporated to dryness to give 6.05 g of the title compound (II-b) partially in the internal hemiacetal form, as a white foam.

$^1$H-NMR (300 MHz, CDCl$_3$, ppm from TMS): 0.96–1.00 (6H, 6s); 2.52–2.72 (1H, m); 4.12 (1H, s); 4.60 (0.25H, m); 5.13 (0.25H, m); 9.72 (0.5H, m).

PREPARATION 3

3-(3β,14β-Dihydroxy-5β-androstane-17β-yl)-propionaldehyde (II-c)

A mixture of 6.00 g of (E)-3β,14β-dihydroxy-5β-pregn-20-ene-21-carboxaldehyde (Fullerton D. S. and Pankaskie M. C., *J. Med. Chem.*, 1976, 19, 1330) and 1.20 g of 5% palladium on charcoal in 1.20 l of ethanol was hydrogenated at room temperature and atmospheric pressure for 30 min. The mixture was then filtered through Celite and ethanol was evaporated to dryness to give 5.95 g of the title compound (II-c) as a white solid.

$^1$H-NMR (300 MHz, CDCl$_3$, ppm from TMS): 0.97 (3H, s); 0.98 (3H, s); 2.20–2.53 (2H, m); 4.12 (1H, s); 9.73 (1H, m).

PREPARATION 4

(E)-3β,14β,17α-Trihydroxy-5β-pregn-20-ene-21-carboxalde-hyde (II-d)

To a solution of 18.40 g of methyl (E)-3β,14β-dihydroxy-5β-pregn-20-ene-21-carboxylate (Boutagy J. and Thomas R., *Aust. J. Pharm. Sci*, 1972, NS1, 67) in 200 ml of dioxane 16.00 g of selenium dioxide were added under nitrogen. The mixture was refluxed for 4 hrs, kept at room temperature overnight and then filtered. The solvent was removed under reduced pressure. Water was added to the crude product and the mixture was filtered to give 13.60 g of methyl (E)-3β,14β,17α-trihydroxy-5β-pregn-20-ene-21-carboxylate as a pale yellow solid.

$^1$H-NMR (300 MHz, CDCl$_3$, ppm from TMS): 0.80 (3H, s); 0.92 (3H, s); 3.69 (3H, s); 4.12 (1H, s); 5.99 (1H, d); 7.65 (1H, d).

13.55 g of methyl (E)-3β,14β,17α-trihydroxy-5β-pregn-20-ene-21-carboxylate were reacted first with i-Bu$_2$AlH and then with MnO$_2$, following the procedure described in Prepn. 1, to give 6.08 g of the title compound (II-d) as a pale yellow solid.

$^1$H-NMR (300 MHz, DMSO-d$_6$, ppm from TMS): 0.69 (3H, s); 0.87 (3H, s); 3.89 (1H, m); 4.16 (1H, s); 4.19 (1H, d); 4.33 (1H, s); 6.11 (1H, dd); 7.68 (1H, d); 9.50 (1H, d).

PREPARATION 5

(E,E)-5-(3β,14β,17α-Trihydroxy-5β-androstane-17β-yl)-2,4-pentadienal (II-e)

To a suspension of 0.28 g of sodium hydride (60% dispersion in mineral oil) in 30 ml of dry tetrahydrofuran, 1.20 ml of trimethyl phosphonoacetate were added dropwise under nitrogen atmosphere at room temperature. The mixture was stirred for 15 min and then a solution of 1.60 g of (E)-3β,14β,17α-trihydroxy-5β-pregn-20-ene-21-carboxaldehyde (Prepn. 4) in 30 ml of dry tetrahydrofuran was added dropwise. After 30 min the reaction was neutralized with aqueous sodium dihydrogenphosphate and extracted with ethyl acetate. The organic layer was dried over anhydrous sodium sulfate and evaporated to dryness to give 1.80 g of methyl (E,E)-5-(3β,14β,17α-trihydroxy-5β-androstane-17β-yl)-2,4-pentadienoate.

$^1$H-NMR (300 MHz, CDCl$_3$, ppm from TMS): 0.82 (3H, s); 0.90 (3H, s); 3.70 (3H, s); 4.12 (1H, s); 6.09 (1H, d); 6.36 (1H, d); 6.98 (1H, dd); 7.85 (1H, dd).

5.00 g of methyl (E,E)-5-(3β,14β,17α-trihydroxy-5β-androstane-17β-yl)-2,4-pentadienoate were reacted first with i-Bu$_2$AlH and then with MnO$_2$, following the procedure described in Prepn. 1, to give 0.80 g of the title compound (II-e) as a white foam.

$^1$H-NMR (300 MHz, DMSO-d$_6$, ppm from TMS): 0.70 (3H, s); 0.87 (3H, s); 3.88 (1H, m); 4.12 (1H, s); 4.14 (1H, d); 4.32 (1H, s); 6.05 (1H, dd); 6.20 (1H, d); 6.64 (1H, dd); 7.75 (1H, dd); 9.50 (1H, d).

PREPARATION 6

3β,14β-17α-Trihydroxy-5β-androstane-17β-ylacetaldehyde (II-f)

To a solution of 9.00 g of methyl (E)-3β,14β-dihydroxy-5β-pregn-20-ene-21-carboxylate (Boutagy J. and Thomas R., *Aust. J. Pharm. Sci.*, 1972, NS1, 67) in 40 ml of pyridine, 0.04 g of 4-dimethylaminopyridine and 11.5 ml of acetic anhydride were added at room temperature, under nitrogen atmosphere. After 4 hrs the reaction was concentrated under reduced pressure, neutralized with aqueous sodium dihydrogenphosphate and then extracted with ethyl acetate. The organic layer was dried over anhydrous sodium sulfate and evaporated to dryness to give 9.05 g of methyl (E)-3β-acetoxy-14β-hydroxy-5β-pregn-20-ene-21-carboxylate.

$^1$H-NMR (300 MHz, CDCl$_3$, ppm from TMS): 0.86 (3H, s); 0.98 (3H, s); 2.05 (3H, s); 3.70 (3H, s); 5.08 (1H, s); 5.62 (1H, d); 7.15 (1H, dd).

A mixture of 9.00 g of methyl (E)-3β-acetoxy-14β-hydroxy-5β-pregn-20-ene-21-carboxylate and 7.00 g of selenium dioxide in 100 ml of dioxane was stirred at reflux temperature under nitrogen. After 3 hrs the reaction was cooled and poured into an aqueous sodium hydrogencarbonate solution and extracted with methylene chloride. The organic layer was dried over anhydrous sodium sulfate and evaporated to dryness. The crude product was purified by flash-chromatography (SiO$_2$) using ethyl acetate/n-hexane 4/6 as the eluant to give 4.80 g of methyl (E)-3β-acetoxy-14β,17α-hydroxy-5β-pregn-20-ene-21-carboxylate.

$^1$H-NMR (300 MHz, CDCl$_3$, ppm from TMS); 0.80 (3H, s); 0.98 (3H, s); 2.05 (3H, s); 3.73 (3H, s); 5.08 (1H, s); 6.00 (1H, d); 7.65 (1H, dd).

A solution of 4.75 g of methyl (E)-3β-acetoxy-14β,17α-dihydroxy-5β-pregn-20-ene-21-carboxylate in 100 ml of ethyl acetate and 200 ml of methanol was ozonized at −78° C. for 30 min. The reaction was allowed to warm to room temperature, and nitrogen was bubbled for 30 min. The solution was added with 3.0 ml of tetrahydrothiophene and stirred at room temperature for 2 hrs. The solvent was removed under reduced pressure and the crude product was purified by flash-chromatography (SiO$_2$) using ethyl acetate/n-hexane 4/6 as the eluant to give 2.60 g of 3β-acetoxy-14β,17α-dihydroxy-5β-androstane-17β-carboxaldehyde.

$^1$H-NMR (300 MHz, CDCl$_3$, ppm from TMS): 0.79 (3H, s); 0.99 (3H, s); 2.06 (3H, s); 10.00 (1H, s).

A mixture of 2.50 g of 3β-acetoxy-14β,17α-dihydroxy-5β-androstane-17β-carboxaldehyde, 0.80 ml of nitromethane and 0.35 g of potassium fluoride in 40 ml of iso-propanol was stirred at room temperature. After 20 hrs the solvent was removed under reduced pressure, the residue was taken up with water and extracted with ethyl acetate. The organic layer was dried over anhydrous sodium sulfate and evaporated to dryness. The residue was dissolved in dry tetrahydrofuran, 1.5 ml of acetic anhydride and 0.10 g of 4-dimethylaminopyridine were added under nitrogen. After stirring at room temperature for 20 hrs, the solvent was evaporated. The residue was dissolved in 100 ml of diethyl ether and 50 ml of ethanol. 0.50 g of sodium borohydride were added. After 1 hr the reaction was quenched with aqueous sodium dihydrogenphosphate and extracted with methylene chloride. The organic layer was dried over anhydrous sodium sulfate and evaporated to dryness to give 2.30 g of 3β-acetoxy-21-nitro-5β-pregnane-14β,17α-diol.

$^1$H-NMR (300 MHz, CDCl$_3$, ppm from TMS): 0.96 (3H, s); 1.00 (3H, s); 2.07 (3H, s); 4.19–4.39 (2H, m); 5.09 (1H, s).

A solution of 2.25 g of 3β-acetoxy-21-nitro-5β-pregnane-14β,17α-diol and 8.00 g of triphenylphosphine in 80 ml of dry methylene chloride was kept at 0° C. under nitrogen: 4.0 ml of diethyl azodicarboxylate were added dropwise during 1 hr. After 2 hrs the solvent was removed under reduced pressure and the residue was purified by flash-chromatography (SiO$_2$) using methylene chloride/diethyl ether 95/5 as the eluant to give 2.40 g of 3β-acetoxy-14β,17α-dihydroxy-5β-pregnane-21-nitrile.

$^1$H-NMR (300 MHz, CDCl$_3$, ppm in TMS): 0.88 (3H, s); 0.92 (3H, s); 1.99 (3H, s); 2.40–2.62 (2H, m); 5.09 (1H, s).

A solution of 2.35 g of 3β-acetoxy-14β,17α-dihydroxy-5β-pregnane-21-nitrile in 50 ml of methanol, 50 ml of tetrahydrofuran and 28 ml of 1N NaOH was stirred at room temperature for 20 hrs. The mixture was then neutralized with sodium dihydrogenphosphate and extracted with ethyl acetate. The organic layer was dried over anhydrous sodium sulfate and the solvent was evaporated to dryness to give 2.30 g of 3β,14β,17α-trihydroxy-5β-pregnane-21-nitrile.

$^1$H-NMR (300 MHz, CDCl$_3$, ppm from TMS): 0.89 (3H, s); 0.94 (3H, s); 2.46–2.70 (2H, m); 4.12 (1H, s).

13.55 g of methyl (E)-3β,14β,17α-trihydroxy-5β-pregn-20-ene-21-carboxylate were reacted with i-Bu$_2$AlH, following the procedure described in Prepn. 2, to give 1.25 g of the title compound (II-f) partially in the internal hemiacetal form, as a white foam.

¹H-NMR (300 MHz, CDCl₃, ppm from TMS): 0.94–1.00 (6H, 6s); 2.49–2.73 (1H, m); 4.12 (1H, s); 4.62 (0.25H, m); 5.10 (0.25H, m); 9.74 (0.5H, m).

PREPARATION 7

3-(3β,14β,17α-Trihydroxy-5β-androstane-17β-yl)-propionaldehyde (II-g)

The title compound (II-g) (1.10 g) was obtained as a white solid starting from (E)-3β,14β,17α-trihydroxy-5β-pregn-20-ene-21-carboxaldehyde (Prepn. 4) (1.15 g) using the same procedure described in Prepn. 3.

¹H-NMR (300 MHz, CDCl₃, ppm from TMS): 0.94 (3H, s); 0.97 (3H, s); 2.20–2.52 (2H, m); 4.12 (1H, s); 9.74 (1H, m).

PREPARATION 8

(E)-3β-[2-(1-Pyrrolidinyl)ethoxy]-21-[2-(1,3-dioxolanyl)]-5β-pregn-20-ene-14β-ol (II-h)

A mixture of 3.00 g of (E)-3β,14β-dihydroxy-5β-pregn-20-ene-21-carboxaldehyde (Fullerton D. S. and Pankaskie M. C., *J. Med. Chem.*, 1976, 19, 1330), 12.0 ml of ethylene glycol, 56 ml of 2,2-dimethyl-1,3-dioxolane and 0.06 g of oxalic acid was heated at 40° C. for 3 days. After cooling the mixture was diluted with 5% aqueous sodium hydrogencarbonate and extracted with ethyl acetate. The organic layer was dried over anhydrous sodium sulfate and evaporated to dryness to give 2.80 g of (E)-21-[2-(1,3-dioxolanyl)]-5β-pregn-20-ene-3β,14β-diol as a white solid.

¹H-NMR (300 MHz, CDCl₃, ppm from TMS): 0.84 (3H, s); 0.93 (3H, s); 3.85–4.05 (4H, m); 4.12 (1H, m); 5.19 (1H, d); 5.28 (1H, dd); 6.12 (1H, dd).

A mixture of 2.70 g of (E)-21-[2-(1,3-dioxolanyl)]5β-pregn-20-ene-3β,14β-diol, 17.0 g of 1-(2-chloroethyl)pyrrolidine and 5.40 g of sodium hydride (55% dispersion in mineral oil) in 300 ml of dry tetrahydrofuran was refluxed for 12 hrs. After cooling, water was added and the mixture was extracted with ethyl acetate; the organic layer was dried over anhydrous sodium sulfate and evaporated to dryness. The crude product was purified by flash-chromatography (SiO₂) using chloroform/methanol 95/5 as eluant; the fractions containing the title compound were collected and evaporated to give 2.50 g of the title compound (II-h) as a dense oil.

¹H-NMR (300 MHz, CDCl₃, ppm from TMS): 0.85 (3H, s); 1.00 (3H, s); 2.85 (6H, m); 3.65 (3H, m); 3.85–4.05 (4H, m); 5.19 (1H, d); 5.27 (1H, dd); 6.11 (1H, dd).

PREPARATION 9

(E)-3β-[3-(1-Pyrrolidinyl)propoxy]-21-[2-(1,3-dioxolanyl)]-5β-pregn-20-ene-14β-ol (II-i)

The title compound (II-i) (1.70 g) was obtained as a dense oil starting from 2.10 g of (E)-21-[2-(1,3-dioxolanyl)]-5β-pregn-20-ene-3β,14β-diol (see Prepn. 8) and 15.0 g of 1-(3-chloropropyl)pyrrolidine using the same procedure described in Prepn. 8.

¹H-NMR (300 MHz, CDCl₃, ppm from TMS): 0.85 (3H, s); 1.00 (3H, s); 2.55 (6H, m); 3.42 (2H, t); 3.62 (1H, m); 3.85–4.05 (4H, m); 5.18 (1H, d); 5.28 (1H, dd); 6.11 (1H, dd).

PREPARATION 10

(E)-3β-(2-Aminoethoxy)-21-[2-(1,3-dioxolanyl)]-5β-pregn-20-ene-14β-ol (II-j)

To a suspension of 7.75 g of NaH (60% dispersion in mineral oil) in 600 ml of dry tetrahydrofuran, 10.5 g of (E)-21-[2-(1,3-dioxolanyl)]-5β-pregn-20-ene-3β,14β-diol (see Prepn. 8) were added at room temperature in a nitrogen atmosphere. The mixture was stirred at reflux for 7 hrs, then 40 ml of bromoacetaldehyde diethylacetal were added and the suspension was stirred at reflux for 4 hrs. After cooling at room temperature 80 ml of water were added cautiously, and tetrahydrofuran was distilled under reduced pressure. The residue was extracted with methylene chloride, the organic layer was dried over anhydrous sodium sulfate and evaporated to dryness. The crude product was purified by flash-chromatography (SiO₂) using n-hexane/ethyl acetate 75/25 as eluant to give 10.25 g of (E)-3β-(2,2-diethoxyethoxy)-21-[2-(1,3-dioxolanyl)]-5β-pregn-20-ene-14β-ol, as a dense oil.

¹H NMR (300 MHz, CDCl₃, ppm from TMS): 0.85 (3H, s); 1.00 (3H, s); 1.23 (6H, t); 3.45–3.50 (2H, m); 3.50–3.80 (5H, m); 3.85–4.05 (4H, m); 4.63 (1H, t); 5.19 (1H, d); 5.29 (1H, dd); 6.13 (1H, dd).

A solution of 10.20 g of 3β-(2,2-diethoxyethoxy)-17β-(2-(1,3-dioxolanyl))-5β-androstan-14β-ol, in 820 ml of dioxane and 640 ml of a saturated aqueous solution of tartaric acid was heated at 70° C. for 2 hrs in a nitrogen atmosphere. After cooling at room temperature, 300 ml of water were added and the mixture was extracted with methylene chloride. The organic layer was washed with water, dried over anhydrous sodium sulfate and evaporated to dryness. The crude product was purified by flash-chromatography (SiO₂) using as eluant n-hexane/ethyl acetate 65/35 to give 3.25 g of (E)-3β-formylmethoxy-21-[2-(1,3-dioxolanyl)]-5β-pregn-20-ene-14β-ol as a white waxy solid.

¹H NMR: (300 MHz, CDCl₃, ppm from TMS): 0.85 (3H, s); 1.02 (3H, s); 3.70 (1H, bs); 3.85–4.05 (4H, m); 4.10 (2H, d); 5.19 (1H, d); 5.28 (1H, dd); 6.13 (1H, dd); 9.75 (1H, t).

To a solution of 3.20 g of (E)-3β-formylmethoxy-21-[2-(1,3-dioxolanyl)]-5β-pregn-20-ene-14β-ol in 300 ml of methanol, 0.90 g of sodium borohydride were added slowly at 0° C. After 30 min. the temperature of the mixture was allowed to warm to 25° C. After 2 hrs 60 ml of water were added, methanol was distilled under reduced pressure, and the residue was extracted with methylene chloride; the organic layer was washed with water, dried over sodium sulfate and evaporated to dryness. The crude product was purified by flash-chromatography (SiO₂) using n-hexane/ethyl acetate 75/25 as eluant to give 2.55 g of (E)-3β-(2-hydroxyethoxy)-21-[2-(1,3-dioxolanyl)]-5β-pregn-20-ene-14β-ol as a white solid.

¹H NMR (300 MHz, CDCl₃, ppm from TMS): 0.86 (3H, s); 1.00 (3H, s); 3.48 (2H, t); 3.62 (1H, bs); 3.70 (2H, t); 3.85–4.05 (4H, m); 5.19 (1H, d); 5.28 (1H, dd); 6.12 (1H, dd).

A solution of 0.90 ml of diethyl azodicarboxylate was added dropwise, under nitrogen, to a solution of 2.55 g of (E)-3β-2-(hydroxyethoxy)-21-[2-(1,3-dioxolanyl)]-5β-pregn-20-ene-14β-ol, 0.90 g of phthalimide and 1.50 g of triphenylphosphine in 23 ml of tetrahydrofuran under stirring at room temperature. After 2 hrs the solvent was removed in vacuo, the crude product was dried over anhydrous sodium sulfate and evaporated to dryness. The crude product was purified by flash-chromatography (SiO₂) using n-hexane/ethyl acetate 75/25 to give 2.50 g of (E)-3β-(2-phthalimidoethoxy)-21-[2-(1,3-dioxolanyl)]-5β-pregn-20-ene-14β-ol.

$^1$H NMR (300 MHz, CDCl$_3$, ppm from TMS): 0.85 (3H, s); 1.00 (3H, s); 3.60–3.68 (3H, m); 3.85–4.20 (6H, m); 5.19 (1H, d); 5.28 (1H, dd); 6.12 (1H, dd); 7.70–7.75 (2H, m); 7.80–7.90 (2H, m).

To a solution of 2.50 g of 3β-(2-phthalimidoethoxy)-17β-(2-(1,3-dioxolanyl))-5β-androstan-14β-ol in 80 ml of ethanol (96%) 0.75 ml of hydrazine hydrate were added at room temperature. The mixture was stirred at reflux for 4 hrs, then 20 ml of water were added and the ethanol distilled under reduced pressure. The residue was extracted with methylene chloride; the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 1.35 g of the title compound (II-j) as a white solid.

$^1$H NMR: (300 MHz, CDCl$_3$, ppm from TMS): 0.85 (3H, s); 1.02 (3H, s); 2.84 (2H, t); 3.40 (2H, m); 3.65 (1H, bs); 3.85–4.05 (4H, m); 5.19 (1H, d); 5.27 (1H, dd); 6.12 (1H, dd).

PREPARATION 11

(E)-3β-(3-Aminopropoxy)-21-[2-(1,3-dioxolanyl)]-5β-pregn-20-ene-14β-ol (II-k)

A solution of 12.00 g of 3β,14β-dihydroxy-5β-androstane-17β-carboxaldehyde (Boutagy J. and Thomas R., *Aust. J. Chem.*, 1971, 24, 2723), 1.60 g of oxalic acid and 20.00 ml of ethylene glycol in 240 ml of acetonitrile was stirred at room temperature for 24 hrs. After basifying with an aqueous sodium hydrogencarbonate solution the mixture was extracted with ethyl acetate; the organic layer was dried over anhydrous sodium sulfate and evaporated to dryness to give 13.10 g of 17β-(2-(1,3-dioxolanyl))-5β-androstane-3β,14β-diol as a dense oil.

$^1$H-NMR (300 MHz, CDCl$_3$, ppm from TMS): 0.98 (3H, s); 1.05 (3H, s); 3.80–4.20 (5H, m); 4.98 (1H, d).

To a solution of 13.05 of 17β-(2-(1,3-dioxolanyl))-5β-androstan-3β,14β-diol in 100 ml of dry tetrahydrofuran, 8.80 g of sodium hydride (60% dispersion in mineral oil) were added under nitrogen atmosphere at room temperature and the resulting mixture was stirred at reflux temperature for 6 hrs. After cooling, 28.0 g of allyl bromide were added and the reflux continued for further 20 hrs. The mixture was quenched with water and the organic solvent was distilled under reduced pressure. The residue was extracted with ethyl acetate; the organic solution was dried over anhydrous sodium sulfate and evaporated to dryness. The residue was purified by flash-chromatography (SiO$_2$) using n-hexane/ethyl acetate 80/20 as eluant to give 11.90 g of 3β-prop-(2-en)oxy-17β-(2-(1,3-dioxolanyl))-5β-androstan-14β-ol as a white solid.

$^1$H-NMR (300 MHz, CDCl$_3$, ppm from TMS): 0.97 (3H, s); 1.04 (3H, s); 3.69 (1H, bs); 3.80–4.20 (6H, m); 4.99 (1H, d); 5.12–5.18 (1H, m); 5.22–5.32 (1H, m); 5.87–6.01 (1H, m).

To a solution of 8.10 g of 9-borabicyclo[3.3.1]nonane in 350 ml of dry tetrahydrofuran, 11.80 g of 3β-prop-(2-en)oxy-17β-(2-(1,3-dioxolanyl))-5β-androstan-14β-ol in 230 ml of tetrahydrofuran were added under nitrogen atmosphere, at room temperature. After stirring for 6 hrs, 12 ml of ethanol, 6.0 ml of 6N sodium hydroxide and 12 ml of 30% hydrogen peroxide were added. The mixture was stirred at 50° C. for 1 hr, quenched with a solution of 18.05 g of potassium carbonate in 400 ml of water and the organic solvent distilled under reduced pressure. The residue was extracted with methylene chloride, the organic solution was dried over anhydrous sodium sulfate and evaporated to dryness. The residue was purified by flash-chromatography (SiO$_2$) using n-hexane/ethyl acetate 70/30 as eluant to give 9.70 g of 3β-(3-hydroxypropoxy)-17β-(2-(1,3-dioxolanyl))-5β-androstan-14β-ol as a white solid.

$^1$H-NMR (300 MHz, CDCl$_3$, ppm from TMS): 0.96 (3H, s); 1.05 (3H, s); 3.57–3.67 (3H, m); 3.80–4.20 (6H, m); 4.98 (1H, d).

A solution of 9.65 g of 3β-(3-hydroxypropoxy)-17β-(2-(1,3-dioxolanyl)-5β-androstan-14β-ol in 100 ml of dioxane was acidified to pH 2.0 with 0.1N hydrochloric acid and stirred for 2 hours. The solution was poured into 5% aqueous sodium hydrogencarbonate and extracted with ethyl acetate. The organic layer was dried over anhydrous sodium sulfate and evaporated to dryness to give 7.80 g of 3β-(3-hydroxypropoxy)-14β-hydroxy-5β-androstan-17β-carboxaldehyde as a white solid.

$^1$H-NMR (300 MHz, CDCl$_3$, ppm from TMS): 0.96 (3H, s); 1.05 (3H, s); 3.55–3.65 (3H, m); 3.80–4.20 (2H, m); 9.23 (1H, d).

7.75 g of 3β-(3-hydroxypropoxy)-14β-hydroxy-5β-androstan-17β-carboxaldehyde were reacted with trimethyl phosphonoacetate in the presence of sodium hydride, using the same procedure described in Prepn. 5, to give 8.55 g of methyl (E)-3β-(3-hydroxypropoxy)-14β-dihydroxy-5β-pregn-20-ene-21-carboxylate as a white foam.

$^1$H-NMR (300 MHz, CDCl$_3$, ppm from TMS): 0.90 (3H, s); 0.96 (3H, s); 3.55–3.65 (3H, m); 3.69 (3H, s); 4.00–4.20 (2H, m); 5.12 (1H, d); 7.18 (1H, dd).

8.50 g of methyl (E)-3β-(3-hydroxypropoxy)-14β-dihydroxy-5β-pregn-20-ene-21-carboxylate were reacted with i-Bu$_2$AlH and successively with MnO$_2$ as described in Prepn. 1, to give 7.95 g of (E)-3β-(3-hydroxypropoxy)-14β-dihydroxy-5β-pregn-20-ene-21-carboxaldehyde.

$^1$H-NMR (300 MHz, CDCl$_3$, ppm from TMS): 0.90 (3H, s); 0.96 (3H, s); 3.55–3.65 (3H, m); 4.00–4.20 (2H, m); 5.91 (1H, d); 7.11 (1H, dd); 9.48 (1H, d).

7.90 g of (E)-3β-(3-hydroxypropoxy)-14β-dihydroxy-5β-pregn-20-ene-21-carboxaldehyde were reacted with ethylene glycol, as described in Prepn. 8, to give 8.50 of (E)-3β-(3-hydroxypropoxy)-21-[2-(1,3-dioxolanyl)]-5β-pregn-20-ene-14β-ol as a white foam $^1$H-NMR (300 MHz, CDCl$_3$, ppm from TMS): 0.90 (3H, s); 0.96 (3H, s); 3.55–3.65 (3H, m); 4.00–4.20 (2H, m); 5.18 (1H, d); 5.29 (1H, dd); 6.12 (1H, dd).

0.65 ml of diethyl azodicarboxylate were added dropwise, under nitrogen, to a solution of 8.45 g of (E)-3β-(3-hydroxypropoxy)-21-[2-(1,3-dioxolanyl)]-5β-pregn-20-ene-14β-ol, 2.75 g of phthalimide and 5.70 g of triphenylphosphine in 80 ml of tetrahydrofuran at room temperature. After 2 hrs the solvent was removed in vacuo, the crude product was dried over anhydrous sodium sulfate and evaporated to dryness. The crude product was purified by flash-chromatography (SiO$_2$) using n-hexane/ethyl acetate 80/20 to give 7.50 g of (E)-3β-(3-phthalimidopropoxy)-21-[2-(1,3-dioxolanyl)]-5β-pregn-20-ene-14β-ol as a white solid.

$^1$H-NMR (300 MHz, CDCl$_3$, ppm for TMS): 0.84 (3H, s); 1.00 (3H, s); 3.38–3.55 (3H, m); 3.80–4.20 (6H, m); 5.19 (1H, d); 5.29 (1H, dd); 6.12 (1H, dd); 7.68–7.75 (2H, m); 7.80–7.90 (2H, m).

To a solution of 7.50 g of (E)-3β-(3-phthalimidopropoxy)-21-[2-(1,3-dioxolanyl)]-5β-pregn-20-ene-14β-ol in 750 ml of ethanol (96%) 3.20 g of hydroazine hydrate were added at room temperature. The mixture was stirred at reflux for 4 hrs. After cooling 10 ml of water were added and the ethanol distilled under reduced pressure. The residue was extracted with methylene chloride, the organic solution was washed with water, dried over anhydrous sodium sulfate and evaporated to dryness. The crude residue was purified by flash-chromatography (SiO₂) using methylene chloride/methanol 90/10 as eluant to give 4.50 g of the title compound (II-k) as a white solid.

¹H-NMR (300 MHz, CDCl₃, ppm from TMS): 0.85 (3H, s); 1.00 (3H, s); 2.60–2.80 (2H, m); 3.30–3.40 (2H, m); 3.58 (1H, bs); 3.85–4.05 (4H, m); 5.19 (1H, d); 5.28 (1H, dd); 6.12 (1H, dd).

PREPARATION 12

3β-[2-(1-Pyrrolidinyl)ethoxy]17β-[2-(1,3-d ioxolanyl)]methyl-5β-androstane-14β-ol (II-l)

The title compound (II-l) (1.70 g) was obtained as a white foam starting from 2.50 g of 3β,14β-dihydroxy-5β-androstane-17β-ylacetaldehyde (II-b) using the same procedure described in Prepn. 8.

¹H-NMR (300 MHz, CDCl₃, ppm from TMS): 0.93 (3H, s); 1.04 (3H, s); 2.85 (6H, m); 3.63 (3H, m); 3.80–4.15 (4H, m); 4.98 (1H, d).

PREPARATION 13

3β-[3-(1-Pyrrolidinyl)propoxy]-17β-[2-(1,3-dioxolanyl)]methyl-5β-androstane-14β-ol (II-m)

The title compound (II-m) (1.40 g) was obtained as a white foam starting from 2.40 g of 3β,14β-dihydroxy-5β-androstane-17β-ylacetaldehyde (II-b) following the same procedure described in Prepn. 8, but using 1-(3-chloropropyl)pyrrolidine in the place of 1-(2-chloroethyl)pyrrolidine.

¹H-NMR (300 MHz, CDCl₃, ppm from TMS): 0.93 (3H, s); 1.04 (3H, s); 2.55 (6H, m); 3.43 (2H, t); 3.62 (1H, m); 3.80–4.15 (4H, m); 5.00 (1H, d).

PREPARATION 14

(E)-3α,14β-Dihydroxy-5β-pregn-20-ene-21-carboxaldehyde (II-n)

To a solution of 5.00 g (E)-21-[2-(1,3-dioxolanyl)]-5β-pregn-20-ene-3β,14β-diol (see Prepn. 8) in 70 ml of methylene chloride, 2.55 g of 4-methylmorpholine N-oxide. 0.25 g of tetrapropylammonium perruthenate and 4.00 of powdered 4 Å molecular sieves were added at room temperature. After 3 hours the solvent was evaporated to dryness and the crude product purified by flash-chromatography (SiO₂) using n-hexane/ethyl acetate 60/40 as eluant to give 4.55 g of (E)-21-[2-(1,3-dioxolanyl)]-5β-pregn-20-ene-14β-ol-3-one as a white solid.

¹H-NMR (300 MHz, CDCl₃, ppm from TMS): 0.85 (3H, s); 1.02 (3H, s); 2.69 (1H, t); 2.79 (1H, dd); 3.85–4.05 (4H, m); 5.19 (1H, d); 5.29 (1H, dd); 6.12 (1H, dd).

To a solution of 4.50 g of (E)-21-[2-(1,3-dioxolanyl)]-5β-pregn-20-ene-14β-ol-3-ene in 35 ml of dry tetrahydrofuran at −78° C., a solution of 9.60 g of tri-tert-butoxyaluminum hydride in 90 ml of dry tetrahydrofuran was added dropwise. The mixture was stirred for 20 hours, then 35 ml of water were added and the temperature was allowed to rise to 25° C. The mixture was filtered through Celite and the insoluble washed with methanol. The solution was concentrated under reduced pressure and extracted with methylene chloride. The organic layer was dried over sodium sulfate and evaporated to give 4.20 g of (E)-21-[2-(1,3-dioxolanyl)]-5β-pregn-20-ene-3α,14β-diol as a white solid.

¹H-NMR (300 MHz, CDCl₃, ppm from TMS): 0.86 (3H, s); 0.90 (3H, s); 3.69 (1H, m); 3.85–4.05 (4H, m); 5.20 (1H, d); 5.28 (1H, dd); 6.12 (1H, dd).

A solution of 4.10 g of (E)-21-[2-(1,3-dioxolanyl)]-5β-pregn-20-ene-3α,14β-diol in 40 ml of dioxane was acidified to pH 2.0 with 0.1N hydrochloric acid and stirred for 2 hours. The solution was poured into a 5% aqueous sodium hydrogencarbonate solution and extracted with ethyl acetate. The organic layer was dried over anhydrous sodium sulfate and evaporated to dryness to give 3.40 g of (E)-3α,14β-dihydroxy-5β-pregn-20-ene-21-carboxaldehyde (II-n) as a white solid.

¹H-NMR (300 MHz, CDCl₃, ppm from TMS): 0.85 (3H, s); 0.92 (3H, s); 2.40–2.50 (1H, m); 3.68 (1H, m); 5.90 (1H, d); 7.10 (1H, dd); 9.47 (1H, d).

PREPARATION 15

(3α,14β-Dihydroxy-5β-androstan-17β-yl)acetaldehyde (II-o)

The title compound (II-o) (1.70 g) was obtained as a white foam starting from 2.50 g of 17β-[2-(1,3-dioxolanyl)]methyl-5β-androstane-3β,14β-diol (prepared as described in Prepn. 8 starting from 3β,14β-dihydroxy-5β-androstane-17β-ylacetaldehyde (II-b)) using the same procedure described in Prepn. 14.

¹H-NMR (300 MHz, ppm from TMS): 0.85–1.00 (6H, 6s); 2.52–2.72 (1H, m); 3.68 (1H, m); 4.60 (0.25H, m); 5.13 (0.25H, m); 9.72 (0.5H, m).

We claim:

1. A 17-aminomethylalkenyl- and 17-iminoalkyl-14β-hydroxy-5β-androstane derivative of general formula (I):

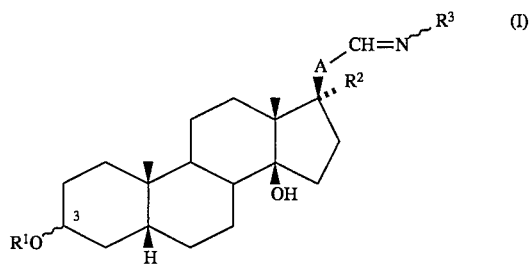

wherein:

the symbol ⁓ means α or β configuration or a Z or E configuration;

A represents $(CH_2)_m$ or $-(CH=CH)_n-$;

m represents an integer number from 1 to 6;

n represents an integer number from 1 to 3;

R¹ represents hydrogen, C2–C4 alkyl unsubstituted or substituted by NR⁴R⁵ wherein R⁴ and R⁵, which may be the same or different, represent hydrogen, C1–C4 alkyl or R⁴ and R⁵ may form, when taken together with the nitrogen atom, a five- or six-membered heterocyclic ring optionally containing one or more further heteroatoms selected from oxygen and nitrogen;

$R^2$ represents hydrogen or hydroxy;

$R^3$ represents $NHC(=X)NR^6R^7$ or $OR^8$ wherein $R^6$ and $R^7$, which may be the same or different, represent hydrogen, methyl or C2–C4 alkyl unsubstituted or substituted by $NR^4R^5$ wherein $R^4$ and $R^5$ have the previously defined meanings;

$R^8$ represents hydrogen; methyl; C2–C6 alkyl, unsubstituted or substituted by one or more $NR^4R^5$ or $NHC(=NH)NH_2$, wherein $R^4$ and $R^5$ have the previously defined meanings;

X represents O, S or N⁓$R^9$;

$R^9$ represents hydrogen, methyl, C2–C4 alkyl, C2–C4 acyl or phenyl, where the C2–C4 alkyl, C2–C4 acyl are unsubstituted or substituted by $NR^4R^5$, wherein $R^4$ and $R^5$ have the previously defined meanings; and $R^6$, $R^7$, and $R^9$, taken two by two, may form, together with the heteroatoms to which they are linked, a five- or six- or seven-membered heterocyclic ring;

or a mixture of α and β isomers at the 3-position; or a mixture of Z and E isomers of the group A—CH=N⁓$R^3$; or a pharmaceutically acceptable salt thereof.

2. A compound according to claim 1, which is selected from:

(E,E)-17β-(3-guanidinoimino-1-propenyl)-5β-androstane-3β,14β-diol (E,E)-17β-[3-(3-methylguanidinoimino)-1-propenyl]-5β-androstane-3β,14β-diol (E,E)-17β-[3-(3,3-dimethylguanidinoimino)-1-propenyl]-5β-androstane-3β,14β-diol (E,E)-17β-[3-(2-imidazolin-2-yl)hydrazono-1-propenyl]-5β-androstane-3β,14β-diol (E,E)-17β-[3-(1-methyl-2-imidazolin-2-yl)hydrazono-1-propenyl]-5β-androstane-3β,14β-diol (E,E)-17β-[3-(5-oxo-2-imidazolin-2-yl)hydrazono-1-propenyl]-5β-androstane-3β,14β-diol (E,E)-17β-[3-(2-imidazolyl)hydrazono-1-propenyl]-5β-androstane-3β,14β-diol (E,E)-17β-[3-(1,4,5,6-tetrahydro-2-pyrimidinyl)hydrazono-1-propenyl]-5β-androstane-3β,14β-diol (E,E)-17β-{3-[3-(2-dimethylaminoethyl)guanidinoimino]-1-propenyl}-5β-androstane-3β,14β-diol (E,E)-17β-[3-(3-phenyl)guanidinoimino-1-propenyl]-5β-androstane-3β,14β-diol (E,E)-17β-(3-semicarbazono-1-propenyl)-5β-androstane-3β,14β-diol (E,E)-17β-(3-thiosemicarbazono-1-propenyl)-5β-androstane-3β,14β-diol (E,E)-17β-(3-hydroxyimino-1-propenyl)-5β-androstane-3β,14β-diol (E,E)-17β-(3-methoxyimino-1-propenyl)-5β-androstane-3β,14β-diol (E,E)-17β-[3-(2-aminoethoxyimino)-1-propenyl]-5β-androstane-3β,14β-diol (E,E)-17β-[3-(3-aminopropoxyimino)-1-propenyl]-5β-androstane-3β,14β-diol (E,E)-17β-[3-(2-dimethylaminoethoxyimino)-1-propenyl]-5β-androstane-3β,14β-diol (E,E)-17β-[3-(3-dimethylaminopropoxyimino)-1-propenyl]-5β-androstane-3β,14β-diol (E,E)-17β-[3-(2-guanidinoethoxyimino)-1-propenyl]-5β-androstane-3β,14β-diol (E,E)-17β-[3-(3-guanidinopropoxyimino)-1-propenyl]-5β-androstane-3β,14β-diol (E,E,E)-17β-(5-guanidinoimino-1,3-pentadienyl)-5β-androstane-3β,14β-diol (E,E,E)-17β-[5-(3-methylguanidinoimino)-1,3-pentadienyl]-5β-androstane-3β,14β-diol (E,E,E)-17β-[5-(3,3-dimethylguanidinoimino)-1,3-pentadienyl]-5β-androstane-3β,14β-diol (E,E,E)-17β-[5-(2-imidazolin-2-yl)hydrazono-1,3-pentadienyl]-5β-androstane-3β,14β-diol (E,E,E)-17β-[5-(1-methyl-2-imidazolin-2-yl)hydrazono-1,3-pentadienyl]-5β-androstane-3β,14β-diol (E,E,E)-17β-[5-(5-oxo-2-imidazolin-2-yl)hydrazono-1,3-pentadienyl]-5β-androstane-3β,14β-diol (E,E,E)-17β-[5-(2-imidazolyl)hydrazono-1,3-pentadienyl]-5β-androstane-3β,14β-diol (E,E,E)-17β-[5-(1,4,5,6-tetrahydro-2-pyrimidinyl)hydrazono-1,3-pentadienyl]-5β-androstane-3β,14β-diol (E,E,E)-17β-{5-[3-(2-dimethylaminoethyl)guanidinoimino]-1,3-pentadienyl}-5β-androstane-3β,14β-diol (E,E,E)-17β-[5-(3-phenylguanidinoimino)-1,3-pentadienyl]-5β-androstane-3β,14β-diol (E,E,E)-17β-(5-semicarbazono-1,3-pentadienyl)-5β-androstane-3β,14β-diol (E,E,E)-17β-(5-thiosemicarbazono-1,3-pentadienyl)-5β-androstane-3β,14β-diol (E,E,E)-17β-(5-hydroxyimino-1,3-pentadienyl)-5β-androstane-3β,14β-diol (E,E,E)-17β-(5-methoxyimino-1,3-pentadienyl)-5β-androstane-3β,14β-diol (E,E,E)-17β-[5-(2-aminoethoxyimino)-1,3-pentadienyl]-5β-androstane-3β,14β-diol (E,E,E)-17β-[5-(3-aminopropoxyimino)-1,3-pentadienyl]-5β-androstane-3β,14β-diol (E,E,E)-17β-[5-(2-dimethylaminoethoxyimino)-1,3-pentadienyl]-5β-androstane-3β,14β-diol (E,E,E)-17β-[5-(3-dimethylaminopropoxyimino)-1,3-pentadienyl]-5β-androstane-3β,14β-diol (E,E,E)-17β-[5-(2-guanidinoethoxyimino)-1,3-pentadienyl]-5β-androstane-3β,14β-diol (E,E,E)-17β-[5-(3-guanidinopropoxyimino)-1,3-pentadienyl]-5β-androstane-3β,14β-diol (E)-17β-(2-guanidinoimino)ethyl-5β-androstane-3β,14β-diol (E)-17β-[2-(3-methylguanidinoimino)ethyl]-5β-androstane-3β,14β-diol (E)-17β-[2-(3,3-dimethylguanidinoimino)ethyl]-5β-androstane-3β,14β-diol (E)-17β-[2-(2-imidazolin-2-yl)hydrazonoethyl]-5β-androstane-3β,14β-diol (E)-17β-[2-(1-methyl-2-imidazolin-2-yl)hydrazonoethyl]-5β-androstane-3β,14β-diol (E)-17β-[2-(5-oxo-2-imidazolin-2-yl)hydrazonoethyl]-5β-androstane-3β,14β-diol (E)-17β-[2-(2-imidazolyl)hydrazonoethyl]-5β-androstane-3β,14β-diol (E)-17β-[2-(1,4,5,6-tetrahydro-2-pyrimidinyl)hydrazonoethyl]-5β-androstane-3β,14β-diol (E)-17β-{2-[3-(2-dimethylaminoethyl)guanidinoimino]ethyl}-5β-androstane-3β,14β-diol (E)-17β-[2-(3-phenylguanidinoimino)ethyl]-5β-androstane-3β,14β-diol (E)-17β-(2-semicarbazonoethyl)-5β-androstane-3β,14β-diol (E)-17β-(2-thiosemicarbazonoethyl)-5β-androstane-3β,14β-diol (E)-17β-(2-hydroxyiminoethyl)-5β-androstane-3β,14β-diol (E)-17β-(2-methoxyiminoethyl)-5β-androstane-3β,14β-diol (E)-17β-[2-(2-aminoethoxyimino)ethyl]-5β-androstane-3β,14β-diol (E)-17β-[2-(3-aminopropoxyimino)ethyl]-5β-androstane-3β,14β-diol (E)-17β-[2-(2-dimethylaminoethoxyimino)ethyl]-5β-androstane-3β,14β-diol (E)-17β-[2-(3-dimethylaminopropoxyimino)ethyl]-5β-androstane-3β,14β-diol (E)-17β-[2-(2-guanidinoethoxyimino)ethyl]-5β-androstane-3β,14β-diol (E)-17β-[2-(3-guanidinopropoxyimino)ethyl]-5β-androstane-3β,14β-diol (E)-17β-(3-guanidinoiminopropyl)-5β-androstane-3β,14β-diol (E)-17β-[3-(3-methylguanidinoimino)propyl]-5β-androstane-3β,14β-diol (E)-17β-[3-(3,3-dimethylguanidinoimino)propyl]-5β-androstane-3β,14β-diol (E)-17β-[3-(2-imidazolin-2-yl)hydrazonopropyl]-5β-androstane-3β,14β-diol (E)-17β-[3-(2-imidazolyl)hydrazonopropyl]-5β-androstane-3β,14β-diol (E)-17β-[3-(1-methyl-2-imidazolin-2-yl)hydrazonopropyl]-5β-androstane-3β,14β-diol (E)-17β-[3-(5-oxo-2-imidazolin-2-yl)hydrazonopropyl]-5β-androstane-3β,14β-diol (E)-17β-[3-(1,4,5,6-tetrahydro-2-pyrimidinyl)hydrazonopropyl]-5β-androstane-3β,14β-diol (E)-17β-{3-[3-(2-dimethylaminoethyl)guanidinoimino]propyl}-5β-androstane-3β,14β-diol (E)-17β-[3-(3-phenylguanidinoimino)propyl]-5β-androstane-3β,14β-diol (E)-17β-(3-semicarbazonopropyl)-5β-androstane-3β,14β-diol (E)-17β-(3-thiosemicarbazonopropyl)-5β-androstane-3β,14β-diol (E)-17β-(3-hydroxyiminopropyl)-5β-androstane-3β,14β-diol (E)-17β-(3-methoxyiminopropyl)-5β-androstane-3β,14β-diol (E)-17β-[3-(2-aminoethoxyimino)propyl]-5β-androstane-3β,14β-diol (E)-17β-[3-(3-aminopropoxyimino)propyl]-5β-androstane-3β,14β-diol (E)-17β-[3-(2-dimethylaminoethoxyimino)propyl]-5β-androstane-3β,14β-diol (E)-17β-[3-(3-dimethylaminopropoxyimino)propyl]-5β-androstane-3β,14β-diol (E)-17β-[3-(2-guanidinoethoxyimino)propyl]-5β-androstane-3β,14β-diol (E)-17β-[3-(3-guanidinopropoxyimino)propyl]-5β-androstane-3β,14β-diol and where there are the (E) isomers also the corresponding (Z) isomers;

and the corresponding 17α-hydroxy compounds of the compounds mentioned above;

and the corresponding 3β-(3-aminopropyl), 3β-(3-dimethylaminopropyl), 3β-(3-diethylaminopropyl), 3β-(3-(1-pyrrolidinyl)propyl), 3β-(2-aminoethyl), 3β-(2-dimethylaminoethyl), 3β-(2-diethylaminoethyl) and 3β-(2-(1-pyrrolidinyl)ethyl) ethers of the compounds mentioned above;

and the corresponding 3α-hydroxy compounds of the 3β-hydroxy derivatives;

and the corresponding 3α-(3-aminopropyl), 3α-(3-dimethylaminopropyl), 3α-(3-diethylaminopropyl), 3α-(3-(1-pyrrolidinyl)propyl), 3α-(2-aminoethyl), 3α-(2-dimethylaminoethyl), 3α-(2-diethylaminoethyl) and 3α-(2-(1-pyrrolidinyl)ethyl) ethers of the compounds mentioned above.

3. A pharmaceutical composition containing a compound of general formula (I) as defined in claim 1 with a pharmaceutically acceptable carrier and/or diluent.

* * * * *